US011384368B2

(12) United States Patent
De Waal et al.

(10) Patent No.: US 11,384,368 B2
(45) Date of Patent: *Jul. 12, 2022

(54) GLYCEROL FREE ETHANOL PRODUCTION

(71) Applicant: DSM IP ASSETS B.V., Heerlen (NL)

(72) Inventors: Paulus Petrus De Waal, Echt (NL); Ingrid Maria Vugt-Van Lutz, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/651,212

(22) PCT Filed: Sep. 25, 2018

(86) PCT No.: PCT/EP2018/075958
§ 371 (c)(1),
(2) Date: Mar. 26, 2020

(87) PCT Pub. No.: WO2019/063542
PCT Pub. Date: Apr. 4, 2019

(65) Prior Publication Data
US 2020/0239914 A1 Jul. 30, 2020

(30) Foreign Application Priority Data

Sep. 29, 2017 (EP) ..................... 17193914

(51) Int. Cl.
| *C12P 7/10* | (2006.01) |
| *C12N 9/04* | (2006.01) |
| *C12N 9/34* | (2006.01) |
| *C12N 9/88* | (2006.01) |

(52) U.S. Cl.
CPC .............. *C12P 7/10* (2013.01); *C12N 9/0006* (2013.01); *C12N 9/2428* (2013.01); *C12N 9/88* (2013.01); *C12Y 101/01008* (2013.01); *C12Y 101/05003* (2013.01); *C12Y 302/0102* (2013.01); *C12Y 302/01003* (2013.01); *C12Y 401/01039* (2013.01); *C12P 2203/00* (2013.01)

(58) Field of Classification Search
None
See application file for complete search history.

(56) References Cited

U.S. PATENT DOCUMENTS

| 9,988,649 B2 | 6/2018 | De Bont et al. | |
| 10,450,588 B2 | 10/2019 | Klaassen et al. | |
| 2015/0176032 A1 | 6/2015 | De Bont et al. | |
| 2015/0353942 A1* | 12/2015 | Van Maris | C12P 7/62 435/106 |
| 2016/0194669 A1* | 7/2016 | Argyros | C12N 9/0006 435/161 |
| 2016/0208291 A1 | 7/2016 | Klaassen et al. | |
| 2018/0251798 A1 | 9/2018 | De Bont et al. | |
| 2019/0309268 A1 | 10/2019 | De Waal et al. | |
| 2019/0330664 A1 | 10/2019 | Klaassen et al. | |

FOREIGN PATENT DOCUMENTS

| WO | 2013081456 A2 | 6/2013 | |
| WO | 2014129898 A2 | 8/2014 | |
| WO | 2015028582 A2 | 3/2015 | |
| WO | 2017077504 A1 | 5/2017 | |
| WO | 2018114762 A1 | 6/2018 | |
| WO | WO-2018114762 A1 * | 6/2018 | ..... C12Y 101/05003 |

OTHER PUBLICATIONS

Viktor et al.,Raw starch conversion by *Saccharomyces cerevisiae* expressing Aspergillus tubingensis amylases, Biotechnol. Biofuels 6, 2013, 167. (Year: 2013).*
European Patent Application No. 16206564.3 filed Dec. 23, 2016. (Year: 2016).*
GenBank, Accession No. AY528665.1, 2005, www.ncbi.nlm.nih.gov. (Year: 2005).*
GenBank, Accession No. XP_007380558.1, 2014, www.ncbi.nlm.nih.gov. (Year: 2014).*
Klein et al., Towards the exploitation of glycerol's high reducing power in *Saccharomyces cerevisiae*-based bioprocesses, Metabolic Eng. 38, 2016, 464-72. (Year: 2016).*
Li et al., Engineered yeast with a CO2-fixation pathway to improve the bio-ethanol production from xylose-mixed sugars, Nature Scientific Reports, 7, Mar. 2017, 43875. (Year: 2017).*
Guadalupe-Medina, Victor, H., et al. "Carbon dioxide fixation by Calvin-Cycle enzymes improves ethanol yield in yeast," Biotechnology for biofuels, (2013), vol. 6, No. 125: 1-12.
Jansen, Mickel L.A., et al. "*Saccharomyces cerevisiae* strains for second-generation ethanol production: from academic exploration to industrial implementation," FEMS yeast research, (2017), vol. 17, No. 5: 1-20.
Kumar, Deepak, and Vijay Singh. "Dry-grind processing using amylase corn and superior yeast to reduce the exogenous enzyme requirements in bioethanol production," Biotechnology for biofuels, (2016), vol. 9, No. 228: 1-12.
Nissen, Torben L., et al. "Anaerobic and aerobic batch cultivations of *Saccharomyces cerevisiae* mutants impaired in glycerol synthesis," Yeast, (2000), vol. 16, No. 5: 463-474.
Purkan, P., et al. "Direct conversion of starch to ethanol using recombinant *Saccharomyces cerevisiae* containing glucoamylase gene," In AIP Conference Proceedings, vol. 1888, No. 1, p. 020041. AIP Publishing LLC, 2017.

(Continued)

*Primary Examiner* — Robert B Mondesi
*Assistant Examiner* — Todd M Epstein
(74) *Attorney, Agent, or Firm* — McBee Moore & Vanik IP, LLC; Susan McBee; Kurt Buechle

(57) ABSTRACT

The invention relates to a recombinant yeast comprising a recombinant yeast comprising a nucleotide sequence coding for a glycerol dehydrogenase, a nucleotide sequence coding for a ribulose-1,5-biphosphate carboxylase oxygenase (EC 4.1.1.39); a nucleotide sequence coding for a phosphoribulokinasey (EC 2.7.1.19); a nucleotide sequence allowing the expression of a glucoamylase (EC 3.2.1.20 or 3.2.1.3); and optionally a nucleotide sequence coding for a glycerol transporter. This cell can be used for the production of ethanol and advantageously produces little or no glycerol.

14 Claims, No Drawings

Specification includes a Sequence Listing.

(56) References Cited

OTHER PUBLICATIONS

PCT International Search Report for PCT/EP2018/075958, dated Nov. 12, 2018.
Floudas, D., et al., "Punctularia strigosozonata (strain HHB-11173) (White-rot fungus)," UniParc, (Mar. 2014).

* cited by examiner

SEQUENCE LISTING

<160> NUMBER OF SEQ ID NOS: 19

<210> SEQ ID NO 1
<211> LENGTH: 365
<212> TYPE: PRT
<213> ORGANISM: Klebsiella pneumoniae
<220> FEATURE:
<221> NAME/KEY: MISC_FEATURE
<222> LOCATION: (1)..(365)
<223> OTHER INFORMATION: K. pneumoniae glycerol dehydrogenase
      (Kpne_gldA) amino acid sequence

<400> SEQUENCE: 1

Met Leu Lys Val Ile Gln Ser Pro Ala Lys Tyr Leu Gln Gly Pro Asp

```
1               5                   10                  15
Ala Ala Val Leu Phe Gly Gln Tyr Ala Lys Asn Leu Ala Glu Ser Phe
                20                  25                  30

Phe Val Ile Ala Asp Asp Phe Val Met Lys Leu Ala Gly Glu Lys Val
                35                  40                  45

Val Asn Gly Leu Gln Ser His Asp Ile Arg Cys His Ala Glu Arg Phe
    50                  55                  60

Asn Gly Glu Cys Ser His Ala Glu Ile Asn Arg Leu Met Ala Ile Leu
65                  70                  75                  80

Gln Lys Gln Gly Cys Arg Gly Val Val Gly Ile Gly Gly Lys Thr
                85                  90                  95

Leu Asp Thr Ala Lys Ala Ile Gly Tyr Tyr Gln Lys Leu Pro Val Val
                100                 105                 110

Val Ile Pro Thr Ile Ala Ser Thr Asp Ala Pro Thr Ser Ala Leu Ser
                115                 120                 125

Val Ile Tyr Thr Glu Ala Gly Glu Phe Glu Tyr Leu Ile Tyr Pro
                130                 135                 140

Lys Asn Pro Asp Met Val Val Met Asp Thr Ala Ile Ile Ala Lys Ala
145                 150                 155                 160

Pro Val Arg Leu Leu Val Ser Gly Met Gly Asp Ala Leu Ser Thr Trp
                165                 170                 175

Phe Glu Ala Lys Ala Cys Tyr Asp Ala Arg Ala Thr Ser Met Ala Gly
                180                 185                 190

Gly Gln Ser Thr Glu Ala Ala Leu Ser Leu Ala Arg Leu Cys Tyr Asp
                195                 200                 205

Thr Leu Leu Ala Glu Gly Glu Lys Ala Arg Leu Ala Ala Gln Ala Gly
    210                 215                 220

Val Val Thr Glu Ala Leu Glu Arg Ile Ile Glu Ala Asn Thr Tyr Leu
225                 230                 235                 240

Ser Gly Ile Gly Phe Glu Ser Ser Gly Leu Ala Ala Ala His Ala Ile
                245                 250                 255

His Asn Gly Phe Thr Ile Leu Glu Glu Cys His His Leu Tyr His Gly
                260                 265                 270

Glu Lys Val Ala Phe Gly Thr Leu Ala Gln Leu Val Leu Gln Asn Ser
                275                 280                 285

Pro Met Asp Glu Ile Glu Thr Val Leu Gly Phe Cys Gln Arg Val Gly
                290                 295                 300

Leu Pro Val Thr Leu Ala Gln Met Gly Val Lys Glu Gly Ile Asp Ala
305                 310                 315                 320

Lys Ile Ala Ala Val Ala Lys Ala Thr Cys Ala Glu Gly Glu Thr Ile
                325                 330                 335

His Asn Met Pro Phe Ala Val Thr Pro Glu Ser Val His Ala Ala Ile
                340                 345                 350

Leu Thr Ala Asp Leu Leu Gly Gln Gln Trp Leu Ala Arg
                355                 360                 365

<210> SEQ ID NO 2
<211> LENGTH: 367
<212> TYPE: PRT
<213> ORGANISM: Enterococcus aerogenes
<220> FEATURE:
<221> NAME/KEY: MISC_FEATURE
<222> LOCATION: (1)..(367)
<223> OTHER INFORMATION: E. aerogenes glycerol dehydrogenase (Eaer_gldA)
      amino acid sequence
```

<400> SEQUENCE: 2

```
Met Asp Arg Ile Ile Gln Ser Pro Gly Lys Tyr Ile Gln Ala Gly
1               5                   10                  15

Ala Ile Lys Arg Leu Gly Glu Tyr Leu Lys Pro Leu Ala Glu Arg Trp
            20                  25                  30

Leu Ile Ile Gly Asp Lys Phe Val Leu Gly Phe Ala Glu Glu Gln Leu
            35                  40                  45

Arg Thr Ser Leu Gly Gly Ala Gly Leu Val Ala Glu Ile Ala Pro Phe
        50                  55                  60

Gly Gly Glu Cys Ser Gln Asn Glu Ile Asn Arg Leu Arg Asp Ile Ala
65                  70                  75                  80

Ser Ser Ala Gln Cys His Ala Val Leu Gly Ile Gly Gly Lys Thr
                85                  90                  95

Leu Asp Thr Ala Lys Ala Leu Ala His Tyr Met His Leu Pro Val Val
                100                 105                 110

Val Ala Pro Thr Ile Ala Ser Thr Asp Ala Pro Cys Ser Ala Leu Ser
            115                 120                 125

Val Ile Tyr Thr Asp Asp Gly Glu Phe Glu Ser Tyr Leu Met Leu Pro
        130                 135                 140

His Asn Pro Asn Met Val Val Asp Thr Gln Ile Val Ala Ala Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
                180                 185                 190

Gly Lys Cys Thr Gln Ala Ala Leu Ala Leu Glu Leu Cys Tyr Asn
            195                 200                 205

Thr Leu Val Glu Glu Gly Glu Lys Ala Met Leu Ala Ala Glu Gln His
        210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Ile
                245                 250                 255

His Asn Gly Leu Thr Ala Ile Pro Asp Ala His His Phe Tyr His Gly
                260                 265                 270

Glu Lys Val Ala Phe Gly Thr Leu Thr Gln Leu Val Leu Glu Asn Ala
            275                 280                 285

Pro Val Glu Glu Ile Glu Thr Ala Ala Ala Leu Cys His Ser Val Gly
        290                 295                 300

Leu Pro Ile Thr Leu Ala Gln Leu Asp Ile Lys Gly Asp Ile Pro Ala
305                 310                 315                 320

Lys Met Arg Thr Val Ala Glu Ala Ala Cys Ala Glu Gly Glu Thr Ile
                325                 330                 335

His Asn Met Pro Gly Gly Ala Cys Ala Asp Gln Val Tyr Ala Ala Leu
            340                 345                 350

Leu Val Ala Asp Gln Tyr Gly Gln Arg Phe Leu Gln Glu Trp Glu
        355                 360                 365
```

<210> SEQ ID NO 3
<211> LENGTH: 364
<212> TYPE: PRT
<213> ORGANISM: Yersinia aldovae
<220> FEATURE:
<221> NAME/KEY: MISC_FEATURE
<222> LOCATION: (1)..(364)

<223> OTHER INFORMATION: Y. aldovae glycerol dehydrogenase (Eaer_gldA) amino acid sequence

<400> SEQUENCE: 3

| | | | | | | | | | | | | | | |
|---|---|---|---|---|---|---|---|---|---|---|---|---|---|---|
| Met | Leu | Lys | Val | Ile | Gln | Ser | Pro | Ser | Lys | Tyr | Ile | Gln | Gly | Ala | Asn |
| 1 | | | | 5 | | | | | 10 | | | | | 15 | |
| Ala | Leu | Gln | Ser | Ile | Gly | Glu | Phe | Ala | Lys | Leu | Leu | Ala | Asn | Asn | Tyr |
| | | | 20 | | | | | 25 | | | | | 30 | | |
| Phe | Ile | Ile | Ala | Asp | Asp | Phe | Val | Met | Lys | Leu | Thr | Ala | Asp | Thr | Val |
| | | 35 | | | | | 40 | | | | | 45 | | | |
| Gly | Thr | Ser | Leu | Gln | Thr | Cys | Glu | Leu | Lys | Ser | His | Phe | Ser | Arg | Phe |
| | 50 | | | | | 55 | | | | | 60 | | | | |
| Asn | Gly | Glu | Cys | Ser | Arg | Gln | Glu | Ile | Glu | Arg | Leu | Thr | Val | Glu | Leu |
| 65 | | | | | 70 | | | | | 75 | | | | | 80 |
| Lys | Lys | Tyr | Gly | Cys | Asn | Gly | Val | Ile | Gly | Ile | Gly | Gly | Gly | Lys | Thr |
| | | | | 85 | | | | | 90 | | | | | 95 | |
| Leu | Asp | Thr | Ala | Lys | Ala | Ile | Ala | His | Tyr | Gln | His | Ile | Pro | Val | Val |
| | | | 100 | | | | | 105 | | | | | 110 | | |
| Val | Val | Pro | Thr | Ile | Ala | Ser | Thr | Asp | Ala | Pro | Thr | Ser | Ala | Leu | Ser |
| | | 115 | | | | | 120 | | | | | 125 | | | |
| Val | Ile | Tyr | Thr | Glu | Gln | Gly | Glu | Phe | Ala | Glu | Tyr | Leu | Ile | Tyr | Pro |
| | 130 | | | | | 135 | | | | | 140 | | | | |
| Lys | Asn | Pro | Asp | Ile | Val | Leu | Met | Asp | Thr | Thr | Ile | Ile | Ala | Lys | Ala |
| 145 | | | | | 150 | | | | | 155 | | | | | 160 |
| Pro | Val | Arg | Leu | Leu | Val | Ala | Gly | Met | Gly | Asp | Ala | Leu | Ser | Thr | Tyr |
| | | | | 165 | | | | | 170 | | | | | 175 | |
| Phe | Glu | Ala | Gln | Ala | Cys | Phe | Asp | Ala | Lys | Ala | Ile | Ser | Met | Ala | Gly |
| | | | 180 | | | | | 185 | | | | | 190 | | |
| Gly | Ala | Ser | Thr | Leu | Ala | Ala | Ile | Thr | Leu | Ala | Arg | Leu | Cys | Tyr | Glu |
| | | | 195 | | | | | 200 | | | | | 205 | | |
| Thr | Leu | Leu | Ala | Glu | Gly | Tyr | Lys | Ala | Lys | Leu | Ala | Val | Glu | Ala | Gly |
| | | 210 | | | | | 215 | | | | | 220 | | | |
| Val | Val | Thr | Glu | Ala | Val | Glu | Arg | Ile | Ile | Glu | Ala | Asn | Thr | Tyr | Leu |
| 225 | | | | | 230 | | | | | 235 | | | | | 240 |
| Ser | Gly | Ile | Gly | Phe | Glu | Ser | Ser | Gly | Leu | Ala | Ala | His | Ala | Ile | |
| | | | | 245 | | | | | 250 | | | | | 255 | |
| His | Asn | Gly | Phe | Thr | Val | Leu | Glu | Glu | Cys | His | His | Leu | Tyr | His | Gly |
| | | | 260 | | | | | 265 | | | | | 270 | | |
| Glu | Lys | Val | Ala | Phe | Gly | Thr | Leu | Thr | Gln | Leu | Val | Leu | Gln | Asn | Ser |
| | | 275 | | | | | 280 | | | | | 285 | | | |
| Ser | Met | Glu | Glu | Ile | Glu | Thr | Val | Leu | Ser | Phe | Cys | Gln | Gln | Leu | Gly |
| | 290 | | | | | 295 | | | | | 300 | | | | |
| Leu | Pro | Ile | Thr | Leu | Ala | Glu | Met | Gly | Val | Thr | Gln | Asp | Leu | Glu | Cys |
| 305 | | | | | 310 | | | | | 315 | | | | | 320 |
| Lys | Ile | Arg | Ala | Val | Ala | Gln | Ala | Ser | Cys | Ala | Glu | Gly | Glu | Thr | Ile |
| | | | | 325 | | | | | 330 | | | | | 335 | |
| His | Asn | Met | Pro | Phe | Lys | Val | Thr | Ala | Asp | Ser | Val | Tyr | Ala | Ala | Ile |
| | | | 340 | | | | | 345 | | | | | 350 | | |
| Ile | Val | Ala | Asp | Arg | Leu | Gly | Gln | Ala | Phe | Leu | Asn | | | | |
| | | | 355 | | | | | 360 | | | | | | | |

<210> SEQ ID NO 4
<211> LENGTH: 572
<212> TYPE: PRT
<213> ORGANISM: Klebsiella pneumoniae

```
<220> FEATURE:
<221> NAME/KEY: MISC_FEATURE
<222> LOCATION: (1)..(572)
<223> OTHER INFORMATION: K. pneumoniae dihydroxyacetone kinase
      (Kpne_dhaK) amino acid sequence

<400> SEQUENCE: 4
```

Met Thr Thr Lys Gln Phe Gln Phe Asp Ser Asp Pro Leu Asn Ser Ala
1               5                   10                  15

Leu Ala Ala Thr Ala Glu Ala Ser Gly Leu Ala Tyr Leu Pro Lys Ser
            20                  25                  30

Lys Val Ile Tyr Tyr Pro Leu Thr Asn Asp Lys Val Thr Leu Ile Ser
            35                  40                  45

Gly Gly Gly Ala Gly His Glu Pro Ala Gln Thr Gly Phe Val Gly Pro
50                  55                  60

Gly Leu Leu Asp Ala Ala Val Ser Gly Gln Ile Phe Ala Ser Pro Ser
65                  70                  75                  80

Thr Lys Gln Ile Ile Ala Gly Val Asn Ala Val Lys Ser Gln Arg Gly
                85                  90                  95

Ser Ile Ile Ile Val Met Asn Tyr Thr Gly Asp Val Ile His Phe Gly
            100                 105                 110

Met Ala Ala Glu Gln Leu Arg Ser Arg Tyr Asp Tyr His Ala Glu Leu
            115                 120                 125

Val Ser Ile Gly Asp Asp Ile Ser Val Asn Lys Lys Ala Gly Arg Arg
            130                 135                 140

Gly Leu Ala Gly Thr Val Leu Val His Lys Ile Ala Gly His Leu Ala
145                 150                 155                 160

Arg Asp Gly Trp Asp Val Gly Val Leu Ala Glu Ala Leu Arg Thr Thr
                165                 170                 175

Ala Ala Asn Leu Ala Thr Val Ala Ser Leu Glu His Cys Thr Val
            180                 185                 190

Pro Gly Arg Lys Phe Glu Thr Glu Leu Ala Ala Asp Glu Met Glu Ile
            195                 200                 205

Gly Met Gly Ile His Asn Glu Pro Gly Val Lys Thr Ile Lys Ile Gly
210                 215                 220

Lys Val Glu Ser Leu Leu Asp Glu Leu Val Asp Lys Phe Glu Pro Ser
225                 230                 235                 240

Lys Gln Asp Phe Val Pro Phe Asn Lys Gly Asp Glu Val Val Leu Leu
                245                 250                 255

Val Asn Ser Leu Gly Gly Val Ser Ser Leu Glu Leu His Ala Ile Ala
            260                 265                 270

Asn Ile Ala Gln Thr Lys Phe Glu Lys Val Leu Gly Val Lys Thr Val
            275                 280                 285

Arg Leu Ile Val Gly Asn Phe Met Ala Ala Phe Asn Gly Pro Gly Phe
290                 295                 300

Ser Leu Thr Leu Leu Asn Val Thr Thr Ala Lys Lys Gly Asn Phe
305                 310                 315                 320

Asp Val Leu Gly Ala Leu Asp Ala Pro Val Ser Thr Ala Ala Trp Pro
                325                 330                 335

Ser Leu Gln Gln Lys Asp Lys Pro Ala Asn Gly Val Gln Glu Glu
            340                 345                 350

Lys Glu Thr Asp Ser Asp Lys Pro Ala Glu Pro Thr Gly Ile Lys Ala
            355                 360                 365

Asp Gly Lys Leu Phe Lys Ala Met Ile Glu Ser Ala Val Asp Asp Leu
370                 375                 380

```
Lys Lys Glu Glu Pro Gln Ile Thr Lys Tyr Asp Thr Ile Ala Gly Asp
385                 390                 395                 400

Gly Asp Cys Gly Glu Thr Leu Leu Ala Gly Asp Gly Ile Leu Asp
            405                 410                 415

Ala Ile Lys Asn Lys Lys Ile Asp Leu Asp Asp Ala Ala Gly Val Ala
        420                 425                 430

Asp Ile Ser His Ile Val Glu Asn Ser Met Gly Gly Thr Ser Gly Gly
            435                 440                 445

Leu Tyr Ser Ile Phe Phe Ser Gly Leu Val Val Gly Ile Lys Glu Thr
        450                 455                 460

Lys Ala Lys Glu Leu Ser Val Asp Val Phe Ala Lys Ala Cys Glu Thr
465                 470                 475                 480

Ala Leu Glu Thr Leu Ser Lys Tyr Thr Gln Ala Arg Val Gly Asp Arg
            485                 490                 495

Thr Leu Met Asp Ala Leu Val Pro Phe Val Glu Thr Leu Ser Lys Thr
            500                 505                 510

Lys Asp Phe Ala Lys Ala Val Glu Ala Ala Arg Lys Gly Ala Asp Glu
        515                 520                 525

Thr Ser Lys Leu Pro Ala Asn Phe Gly Arg Ala Ser Tyr Val Asn Glu
            530                 535                 540

Glu Gly Leu Glu Asn Ile Pro Asp Pro Gly Ala Leu Gly Leu Ala Val
545                 550                 555                 560

Ile Phe Glu Gly Leu Leu Lys Ala Trp Glu Lys Lys
            565                 570

<210> SEQ ID NO 5
<211> LENGTH: 580
<212> TYPE: PRT
<213> ORGANISM: Yarrowia lipolytica
<220> FEATURE:
<221> NAME/KEY: MISC_FEATURE
<222> LOCATION: (1)..(580)
<223> OTHER INFORMATION: Y. lipolytica dihydroxyacetone kinase
      (Ylip_DAK1) amino acid sequence

<400> SEQUENCE: 5

Met Asp Lys His Phe Ile Asn Asp Pro Glu Val Leu Val Leu Asp Gly
1               5                   10                  15

Leu Lys Ser Leu Ala Asp Met Asn Lys Thr Leu Thr Val His Glu Glu
            20                  25                  30

Gly Lys Phe Ile Tyr Phe His Asp Tyr Asn Lys Lys Asn Val Ser Val
        35                  40                  45

Ile Ser Gly Gly Gly Ala Gly His Glu Pro Thr His Ser Ser Phe Val
    50                  55                  60

Gly Lys Gly Met Leu Thr Ala Ala Val Ser Ser Ile Phe Ala Ser
65                  70                  75                  80

Pro Ser Ser Lys Gln Ile Tyr Thr Gly Ile Lys Gln Val Glu Ser Glu
            85                  90                  95

Ala Gly Thr Leu Val Ile Cys Lys Asn Tyr Thr Gly Asp Ile Leu His
        100                 105                 110

Phe Gly Met Ala Leu Glu Lys Gln Arg Thr Ala Gly Lys Lys Ala Glu
        115                 120                 125

Leu Ile Ala Val Ala Asp Asp Val Ser Val Gly Arg Lys Lys Ser Gly
    130                 135                 140

Lys Val Gly Arg Arg Gly Leu Ser Gly Thr Val Leu Val His Lys Ile
145                 150                 155                 160
```

-continued

```
Ala Gly Ala Ala Ala Ala Arg Gly Leu Pro Leu Glu Ala Val Thr Thr
            165                 170                 175

Ile Ala Lys Ala Ala Ile Asp Asn Leu Val Ser Ile Gly Ala Ser Leu
            180                 185                 190

Ala His Val His Val Pro Gly His Glu Pro Ile Ala Lys Glu Asp Glu
            195                 200                 205

Met Lys His Asp Glu Met Glu Leu Gly Met Gly Ile His Asn Glu Pro
            210                 215                 220

Gly Cys Lys Arg Ile Ser Pro Ile Pro Ser Ile Asp Asp Leu Ile Ala
225                 230                 235                 240

Gln Met Leu Lys Gln Met Leu Asp Gln Ser Asp Lys Arg Ala Tyr
            245                 250                 255

Val Lys Ile Glu Gly Asp Asp Glu Val Val Leu Leu Met Asn Asn Leu
            260                 265                 270

Gly Gly Leu Ser Met Leu Glu Phe Ser Ala Ile Ser His Lys Val Lys
            275                 280                 285

Glu Ala Leu Ala Lys Glu Tyr Lys Ile Asn Pro Val Arg Ile Phe Ala
            290                 295                 300

Gly Pro Phe Thr Thr Ser Leu Asn Gly Leu Gly Phe Gly Ile Thr Leu
305                 310                 315                 320

Leu Arg Thr Thr Asp Arg Val Lys Val Glu Gly Glu Tyr Ser Leu
            325                 330                 335

Val Asp Leu Ile Asp Gln Pro Val Glu Ala Ile Gly Trp Pro Leu Cys
            340                 345                 350

Gln Pro Ser Asp Leu Lys Ser Lys Asn Lys Ile Gly Asn Val Ser Ile
            355                 360                 365

Glu Glu Gly Gln Lys Asp Val Lys Ser Pro Val Thr Val Asp Lys Glu
            370                 375                 380

Lys Val Arg Gln Ala Ile Val Asn Ser Met Glu Asn Leu Ile Lys Ala
385                 390                 395                 400

Glu Pro Lys Ile Thr Lys Phe Asp Thr Met Ala Gly Asp Gly Asp Cys
            405                 410                 415

Gly Thr Thr Leu Lys Arg Gly Ala Glu Gly Val Leu Lys Phe Val Lys
            420                 425                 430

Ser Asp Lys Phe Ser Asp Asp Pro Ile Arg Ile Val Arg Asp Ile Ala
            435                 440                 445

Asp Val Ile Glu Asp Asn Met Asp Gly Thr Ser Gly Ala Leu Tyr Ala
450                 455                 460

Ile Phe Phe His Gly Phe Ala Lys Gly Met Lys Asp Thr Leu Glu Lys
465                 470                 475                 480

Ser Lys Asp Ile Ser Ser Lys Thr Trp Ala Ala Gly Leu Lys Val Ala
            485                 490                 495

Leu Asp Thr Leu Phe Lys Tyr Thr Pro Ala Arg Pro Gly Asp Ser Thr
            500                 505                 510

Met Cys Asp Ala Leu Val Pro Phe Glu Thr Phe Val Lys Thr Asn
            515                 520                 525

Asp Leu Asn Ala Ala Val Glu Glu Ala Arg Lys Gly Ala Asp Ala Thr
            530                 535                 540

Ala Asp Met Gln Ala Lys Leu Gly Arg Ala Val Tyr Val Gly Asp Asp
545                 550                 555                 560

Val Lys Val Pro Asp Ala Gly Ala Leu Gly Val Val Ala Ile Val Glu
            565                 570                 575
```

Gly Phe Thr Lys
            580

<210> SEQ ID NO 6
<211> LENGTH: 580
<212> TYPE: PRT
<213> ORGANISM: Schizosaccharomyces pombe
<220> FEATURE:
<221> NAME/KEY: MISC_FEATURE
<222> LOCATION: (1)..(580)
<223> OTHER INFORMATION: S. pombe dihydroxyacetone kinase (Spom_DAK1)
      amino acid sequence

<400> SEQUENCE: 6

Met Asp Lys His Phe Ile Asn Asp Pro Glu Val Leu Val Leu Asp Gly
1               5                   10                  15

Leu Lys Ser Leu Ala Asp Met Asn Lys Thr Leu Thr Val His Glu Glu
            20                  25                  30

Gly Lys Phe Ile Tyr Phe His Asp Tyr Asn Lys Lys Asn Val Ser Val
        35                  40                  45

Ile Ser Gly Gly Gly Ala Gly His Glu Pro Thr His Ser Ser Phe Val
    50                  55                  60

Gly Lys Gly Met Leu Thr Ala Ala Val Ser Gly Ser Ile Phe Ala Ser
65                  70                  75                  80

Pro Ser Ser Lys Gln Ile Tyr Thr Gly Ile Lys Gln Val Glu Ser Glu
                85                  90                  95

Ala Gly Thr Leu Val Ile Cys Lys Asn Tyr Thr Gly Asp Ile Leu His
            100                 105                 110

Phe Gly Met Ala Leu Glu Lys Gln Arg Thr Ala Gly Lys Lys Ala Glu
        115                 120                 125

Leu Ile Ala Val Ala Asp Asp Val Ser Val Gly Arg Lys Lys Ser Gly
    130                 135                 140

Lys Val Gly Arg Arg Gly Leu Ser Gly Thr Val Leu Val His Lys Ile
145                 150                 155                 160

Ala Gly Ala Ala Ala Ala Arg Gly Leu Pro Leu Glu Ala Val Thr Thr
                165                 170                 175

Ile Ala Lys Ala Ala Ile Asp Asn Leu Val Ser Ile Gly Ala Ser Leu
            180                 185                 190

Ala His Val His Val Pro Gly His Glu Pro Ile Ala Lys Glu Asp Glu
        195                 200                 205

Met Lys His Asp Glu Met Glu Leu Gly Met Gly Ile His Asn Glu Pro
    210                 215                 220

Gly Cys Lys Arg Ile Ser Pro Ile Pro Ser Ile Asp Asp Leu Ile Ala
225                 230                 235                 240

Gln Met Leu Lys Gln Met Leu Asp Gln Ser Asp Lys Asp Arg Ala Tyr
                245                 250                 255

Val Lys Ile Glu Gly Asp Asp Glu Val Val Leu Leu Met Asn Asn Leu
            260                 265                 270

Gly Gly Leu Ser Met Leu Glu Phe Ser Ala Ile Ser His Lys Val Lys
        275                 280                 285

Glu Ala Leu Ala Lys Glu Tyr Lys Ile Asn Pro Val Arg Ile Phe Ala
    290                 295                 300

Gly Pro Phe Thr Thr Ser Leu Asn Gly Leu Gly Phe Gly Ile Thr Leu
305                 310                 315                 320

Leu Arg Thr Thr Asp Arg Val Lys Val Glu Gly Glu Glu Tyr Ser Leu
                325                 330                 335

Val Asp Leu Ile Asp Gln Pro Val Glu Ala Ile Gly Trp Pro Leu Cys
              340                 345                 350

Gln Pro Ser Asp Leu Lys Ser Lys Asn Lys Ile Gly Asn Val Ser Ile
        355                 360                 365

Glu Glu Gly Gln Lys Asp Val Lys Ser Pro Val Thr Val Asp Lys Glu
    370                 375                 380

Lys Val Arg Gln Ala Ile Val Asn Ser Met Glu Asn Leu Ile Lys Ala
385                 390                 395                 400

Glu Pro Lys Ile Thr Lys Phe Asp Thr Met Ala Gly Asp Gly Asp Cys
              405                 410                 415

Gly Thr Thr Leu Lys Arg Gly Ala Glu Gly Val Leu Lys Phe Val Lys
              420                 425                 430

Ser Asp Lys Phe Ser Asp Pro Ile Arg Ile Val Arg Asp Ile Ala
        435                 440                 445

Asp Val Ile Glu Asp Asn Met Asp Gly Thr Ser Gly Ala Leu Tyr Ala
        450                 455                 460

Ile Phe Phe His Gly Phe Ala Lys Gly Met Lys Asp Thr Leu Glu Lys
465                 470                 475                 480

Ser Lys Asp Ile Ser Ser Lys Thr Trp Ala Ala Gly Leu Lys Val Ala
              485                 490                 495

Leu Asp Thr Leu Phe Lys Tyr Thr Pro Ala Arg Pro Gly Asp Ser Thr
              500                 505                 510

Met Cys Asp Ala Leu Val Pro Phe Val Glu Thr Phe Val Lys Thr Asn
              515                 520                 525

Asp Leu Asn Ala Ala Val Glu Glu Ala Arg Lys Gly Ala Asp Ala Thr
        530                 535                 540

Ala Asp Met Gln Ala Lys Leu Gly Arg Ala Val Tyr Val Gly Asp Asp
545                 550                 555                 560

Val Lys Val Pro Asp Ala Gly Ala Leu Gly Val Val Ala Ile Val Glu
              565                 570                 575

Gly Phe Thr Lys
          580

<210> SEQ ID NO 7
<211> LENGTH: 291
<212> TYPE: PRT
<213> ORGANISM: Danio rerio
<220> FEATURE:
<221> NAME/KEY: MISC_FEATURE
<222> LOCATION: (1)..(291)
<223> OTHER INFORMATION: D. rerio aquaporin 9 (Drer_T3) amino acid
      sequence

<400> SEQUENCE: 7

Met Glu Tyr Leu Glu Asn Ile Arg Asn Leu Arg Gly Arg Cys Val Leu
1               5                   10                  15

Arg Arg Asp Ile Ile Arg Glu Phe Leu Ala Glu Leu Leu Gly Thr Phe
            20                  25                  30

Val Leu Ile Leu Phe Gly Cys Gly Ser Val Ala Gln Thr Val Leu Ser
        35                  40                  45

Arg Glu Ala Lys Gly Gln Leu Leu Thr Ile His Phe Gly Phe Thr Leu
    50                  55                  60

Gly Val Met Leu Ala Val Tyr Met Ala Gly Gly Val Ser Gly Gly His
65                  70                  75                  80

Val Asn Pro Ala Val Ser Leu Ala Met Val Val Leu Arg Lys Leu Pro
            85                  90                  95

Leu Lys Lys Phe Pro Val Tyr Val Leu Ala Gln Phe Leu Gly Ala Phe
            100                 105                 110

Phe Gly Ser Cys Ala Val Tyr Cys Leu Tyr Tyr Asp Ala Phe Thr Glu
        115                 120                 125

Phe Ala Asn Gly Glu Leu Ala Val Thr Gly Pro Asn Val Thr Ala Gly
    130                 135                 140

Ile Phe Ala Ser Tyr Pro Arg Glu Gly Leu Ser Leu Leu Asn Gly Phe
145                 150                 155                 160

Ile Asp Gln Val Ile Gly Ala Gly Ala Leu Val Leu Cys Ile Leu Ala
                165                 170                 175

Val Val Asp Lys Lys Asn Ile Gly Ala Pro Lys Gly Met Glu Pro Leu
            180                 185                 190

Leu Val Gly Leu Ser Ile Leu Ala Ile Gly Val Ser Met Ala Leu Asn
        195                 200                 205

Cys Gly Tyr Pro Ile Asn Pro Ala Arg Asp Leu Gly Pro Arg Leu Phe
    210                 215                 220

Thr Ala Ile Ala Gly Trp Gly Leu Thr Val Phe Ser Ala Gly Asn Gly
225                 230                 235                 240

Trp Trp Trp Val Pro Val Val Gly Pro Met Val Gly Val Val Gly
                245                 250                 255

Ala Ala Ile Tyr Phe Leu Met Ile Glu Met His His Pro Glu Asn Asp
            260                 265                 270

Lys Asn Leu Glu Asp Asp Asn Ser Leu Lys Asp Lys Tyr Glu Leu Asn
        275                 280                 285

Thr Val Asn
        290

<210> SEQ ID NO 8
<211> LENGTH: 592
<212> TYPE: PRT
<213> ORGANISM: Zygosaccharomyces rouxii
<220> FEATURE:
<221> NAME/KEY: MISC_FEATURE
<222> LOCATION: (1)..(592)
<223> OTHER INFORMATION: Z. rouxii ZYRO0E01210p (Zrou_T5) amino acid
      sequence

<400> SEQUENCE: 8

Met Gly Lys Arg Thr Gln Gly Phe Met Asp Tyr Val Phe Ser Arg Thr
1               5                   10                  15

Ser Thr Ala Gly Leu Lys Gly Ala Arg Leu Arg Tyr Thr Ala Ala Ala
            20                  25                  30

Val Ala Val Ile Gly Phe Ala Leu Phe Gly Tyr Asp Gln Gly Leu Met
        35                  40                  45

Ser Gly Leu Ile Thr Gly Asp Gln Phe Asn Lys Glu Phe Pro Pro Thr
    50                  55                  60

Lys Ser Asn Gly Asp Asn Asp Arg Tyr Ala Ser Val Ile Gln Gly Ala
65                  70                  75                  80

Val Thr Ala Cys Tyr Glu Ile Gly Cys Phe Phe Gly Ser Leu Phe Val
                85                  90                  95

Leu Phe Phe Gly Asp Ala Ile Gly Arg Lys Pro Leu Ile Ile Phe Gly
            100                 105                 110

Ala Ile Ile Val Ile Ile Gly Thr Val Ile Ser Thr Ala Pro Phe His
        115                 120                 125

His Ala Trp Gly Leu Gly Gln Phe Val Val Gly Arg Val Ile Thr Gly
    130                 135                 140

-continued

Val Gly Thr Gly Phe Asn Thr Ser Thr Ile Pro Val Trp Gln Ser Glu
145                 150                 155                 160

Met Thr Lys Pro Asn Ile Arg Gly Ala Met Ile Asn Leu Asp Gly Ser
            165                 170                 175

Val Ile Ala Phe Gly Thr Met Ile Ala Tyr Trp Leu Asp Phe Gly Phe
        180                 185                 190

Ser Phe Ile Asn Ser Ser Val Gln Trp Arg Phe Pro Val Ser Val Gln
    195                 200                 205

Ile Ile Phe Ala Leu Val Leu Leu Phe Gly Ile Val Arg Met Pro Glu
    210                 215                 220

Ser Pro Arg Trp Leu Met Ala Lys Lys Arg Pro Ala Glu Ala Arg Tyr
225                 230                 235                 240

Val Leu Ala Cys Leu Asn Asp Leu Pro Glu Asn Asp Asp Ala Ile Leu
                245                 250                 255

Ala Glu Met Thr Ser Leu His Glu Ala Val Asn Arg Ser Ser Asn Gln
            260                 265                 270

Lys Ser Gln Met Lys Ser Leu Phe Ser Met Gly Lys Gln Gln Asn Phe
        275                 280                 285

Ser Arg Ala Leu Ile Ala Ser Ser Thr Gln Phe Phe Gln Gln Phe Thr
    290                 295                 300

Gly Cys Asn Ala Ala Ile Tyr Tyr Ser Thr Val Leu Phe Gln Thr Thr
305                 310                 315                 320

Val Gln Leu Asp Arg Leu Leu Ala Met Ile Leu Gly Gly Val Phe Ala
                325                 330                 335

Thr Val Tyr Thr Leu Ser Thr Leu Pro Ser Phe Tyr Leu Val Glu Lys
            340                 345                 350

Val Gly Arg Arg Lys Met Phe Phe Gly Ala Leu Gly Gln Gly Ile
        355                 360                 365

Ser Phe Ile Ile Thr Phe Ala Cys Leu Val Asn Pro Thr Lys Gln Asn
    370                 375                 380

Ala Lys Gly Ala Ala Val Gly Leu Tyr Leu Phe Ile Ile Cys Phe Gly
385                 390                 395                 400

Leu Ala Ile Leu Glu Leu Pro Trp Ile Tyr Pro Pro Glu Ile Ala Ser
                405                 410                 415

Met Arg Val Arg Ala Ala Thr Asn Ala Met Ser Thr Cys Thr Asn Trp
            420                 425                 430

Val Thr Asn Phe Ala Val Val Met Phe Thr Pro Val Phe Ile Gln Thr
        435                 440                 445

Ser Gln Trp Gly Cys Tyr Leu Phe Phe Ala Val Met Asn Phe Ile Tyr
    450                 455                 460

Leu Pro Val Ile Phe Phe Phe Tyr Pro Glu Thr Ala Gly Arg Ser Leu
465                 470                 475                 480

Glu Glu Ile Asp Ile Ile Phe Ala Lys Ala His Val Asp Gly Thr Leu
                485                 490                 495

Pro Trp Met Val Ala His Arg Leu Pro Lys Leu Ser Met Thr Glu Val
            500                 505                 510

Glu Asp Tyr Ser Gln Ser Leu Gly Leu His Asp Asp Glu Asn Glu Lys
        515                 520                 525

Glu Glu Tyr Asp Glu Lys Glu Ala Glu Ala Asn Ala Ala Leu Phe Gln
    530                 535                 540

Val Glu Thr Ser Ser Lys Ser Pro Ser Ser Asn Arg Lys Asp Asp Asp
545                 550                 555                 560

Ala Pro Ile Glu His Asn Glu Val Gln Glu Ser Asn Asp Asn Ser Ser 565                 570                 575
Asn Ser Ser Asn Val Glu Ala Pro Ile Pro Val His His Asn Asp Pro
            580                 585                 590

<210> SEQ ID NO 9
<211> LENGTH: 97
<212> TYPE: PRT
<213> ORGANISM: Escherichia coli
<220> FEATURE:
<221> NAME/KEY: MISC_FEATURE
<222> LOCATION: (1)..(97)
<223> OTHER INFORMATION: groES from E. coli

<400> SEQUENCE: 9

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
                85                  90                  95

Ala

<210> SEQ ID NO 10
<211> LENGTH: 548
<212> TYPE: PRT
<213> ORGANISM: Escherichia coli
<220> FEATURE:
<221> NAME/KEY: MISC_FEATURE
<222> LOCATION: (1)..(548)
<223> OTHER INFORMATION: groEL from E. coli

<400> SEQUENCE: 10

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

-continued

```
Leu Ile Ala Glu Ala Met Asp Lys Val Gly Lys Glu Gly Val Ile Thr
            165                 170                 175
Val Glu Asp Gly Thr Gly Leu Gln Asp Glu Leu Asp Val Val Glu Gly
        180                 185                 190
Met Gln Phe Asp Arg Gly Tyr Leu Ser Pro Tyr Phe Ile Asn Lys Pro
    195                 200                 205
Glu Thr Gly Ala Val Glu Leu Glu Ser Pro Phe Ile Leu Leu Ala Asp
210                 215                 220
Lys Lys Ile Ser Asn Ile Arg Glu Met Leu Pro Val Leu Glu Ala Val
225                 230                 235                 240
Ala Lys Ala Gly Lys Pro Leu Leu Ile Ile Ala Glu Asp Val Glu Gly
            245                 250                 255
Glu Ala Leu Ala Thr Leu Val Val Asn Thr Met Arg Gly Ile Val Lys
        260                 265                 270
Val Ala Ala Val Lys Ala Pro Gly Phe Gly Asp Arg Arg Lys Ala Met
    275                 280                 285
Leu Gln Asp Ile Ala Thr Leu Thr Gly Gly Thr Val Ile Ser Glu Glu
290                 295                 300
Ile Gly Met Glu Leu Glu Lys Ala Thr Leu Glu Asp Leu Gly Gln Ala
305                 310                 315                 320
Lys Arg Val Val Ile Asn Lys Asp Thr Thr Thr Ile Ile Asp Gly Val
            325                 330                 335
Gly Glu Glu Ala Ala Ile Gln Gly Arg Val Ala Gln Ile Arg Gln Gln
        340                 345                 350
Ile Glu Glu Ala Thr Ser Asp Tyr Asp Arg Glu Lys Leu Gln Glu Arg
    355                 360                 365
Val Ala Lys Leu Ala Gly Gly Val Ala Val Ile Lys Val Gly Ala Ala
370                 375                 380
Thr Glu Val Glu Met Lys Glu Lys Lys Ala Arg Val Glu Asp Ala Leu
385                 390                 395                 400
His Ala Thr Arg Ala Ala Val Glu Glu Gly Val Val Ala Gly Gly Gly
            405                 410                 415
Val Ala Leu Ile Arg Val Ala Ser Lys Leu Ala Asp Leu Arg Gly Gln
        420                 425                 430
Asn Glu Asp Gln Asn Val Gly Ile Lys Val Ala Leu Arg Ala Met Glu
    435                 440                 445
Ala Pro Leu Arg Gln Ile Val Leu Asn Cys Gly Glu Glu Pro Ser Val
450                 455                 460
Val Ala Asn Thr Val Lys Gly Asp Gly Asn Tyr Gly Tyr Asn Ala
465                 470                 475                 480
Ala Thr Glu Glu Tyr Gly Asn Met Ile Asp Met Gly Ile Leu Asp Pro
            485                 490                 495
Thr Lys Val Thr Arg Ser Ala Leu Gln Tyr Ala Ala Ser Val Ala Gly
        500                 505                 510
Leu Met Ile Thr Thr Glu Cys Met Val Thr Asp Leu Pro Lys Asn Asp
    515                 520                 525
Ala Ala Asp Leu Gly Ala Ala Gly Gly Met Gly Gly Met Gly Gly Met
530                 535                 540
Gly Gly Met Met
545

<210> SEQ ID NO 11
<211> LENGTH: 459
<212> TYPE: PRT
```

-continued

<213> ORGANISM: Thiobacillus denitrificans
<220> FEATURE:
<221> NAME/KEY: MISC_FEATURE
<222> LOCATION: (1)..(459)
<223> OTHER INFORMATION: RubisCO cbbM gene from Thiobacillus
      denitrificans

<400> SEQUENCE: 11

Met Asp Gln Ser Ala Arg Tyr Ala Asp Leu Ser Leu Lys Glu Glu Asp
1               5                   10                  15

Leu Ile Lys Gly Gly Arg His Ile Leu Val Ala Tyr Lys Met Lys Pro
                20                  25                  30

Lys Ser Gly Tyr Gly Tyr Leu Glu Ala Ala His Phe Ala Ala Glu
            35                  40                  45

Ser Ser Thr Gly Thr Asn Val Glu Val Ser Thr Asp Asp Phe Thr
    50                  55                  60

Lys Gly Val Asp Ala Leu Val Tyr Tyr Ile Asp Glu Ala Ser Glu Asp
65                  70                  75                  80

Met Arg Ile Ala Tyr Pro Leu Glu Leu Phe Asp Arg Asn Val Thr Asp
                85                  90                  95

Gly Arg Phe Met Leu Val Ser Phe Leu Thr Leu Ala Ile Gly Asn Asn
            100                 105                 110

Gln Gly Met Gly Asp Ile Glu His Ala Lys Met Ile Asp Phe Tyr Val
        115                 120                 125

Pro Glu Arg Cys Ile Gln Met Phe Asp Gly Pro Ala Thr Asp Ile Ser
    130                 135                 140

Asn Leu Trp Arg Ile Leu Gly Arg Pro Val Val Asn Gly Gly Tyr Ile
145                 150                 155                 160

Ala Gly Thr Ile Ile Lys Pro Lys Leu Gly Leu Arg Pro Glu Pro Phe
                165                 170                 175

Ala Lys Ala Ala Tyr Gln Phe Trp Leu Gly Gly Asp Phe Ile Lys Asn
            180                 185                 190

Asp Glu Pro Gln Gly Asn Gln Val Phe Cys Pro Leu Lys Lys Val Leu
        195                 200                 205

Pro Leu Val Tyr Asp Ala Met Lys Arg Ala Gln Asp Asp Thr Gly Gln
    210                 215                 220

Ala Lys Leu Phe Ser Met Asn Ile Thr Ala Asp Asp His Tyr Glu Met
225                 230                 235                 240

Cys Ala Arg Ala Asp Tyr Ala Leu Glu Val Phe Gly Pro Asp Ala Asp
                245                 250                 255

Lys Leu Ala Phe Leu Val Asp Gly Tyr Val Gly Gly Pro Gly Met Val
            260                 265                 270

Thr Thr Ala Arg Arg Gln Tyr Pro Gly Gln Tyr Leu His Tyr His Arg
        275                 280                 285

Ala Gly His Gly Ala Val Thr Ser Pro Ser Ala Lys Arg Gly Tyr Thr
    290                 295                 300

Ala Phe Val Leu Ala Lys Met Ser Arg Leu Gln Gly Ala Ser Gly Ile
305                 310                 315                 320

His Val Gly Thr Met Gly Tyr Gly Lys Met Glu Gly Glu Gly Asp Asp
                325                 330                 335

Lys Ile Ile Ala Tyr Met Ile Glu Arg Asp Glu Cys Gln Gly Pro Val
            340                 345                 350

Tyr Phe Gln Lys Trp Tyr Gly Met Lys Pro Thr Thr Pro Ile Ile Ser
        355                 360                 365

Gly Gly Met Asn Ala Leu Arg Leu Pro Gly Phe Phe Glu Asn Leu Gly

```
            370                 375                 380
His Gly Asn Val Ile Asn Thr Ala Gly Gly Ser Tyr Gly His Ile
385                 390                 395                 400

Asp Ser Pro Ala Ala Gly Ala Ile Ser Leu Arg Gln Ser Tyr Glu Cys
                405                 410                 415

Trp Lys Gln Gly Ala Asp Pro Ile Glu Phe Ala Lys Glu His Lys Glu
                420                 425                 430

Phe Ala Arg Ala Phe Glu Ser Phe Pro Lys Asp Ala Asp Lys Leu Phe
                435                 440                 445

Pro Gly Trp Arg Glu Lys Leu Gly Val His Ser
450                 455

<210> SEQ ID NO 12
<211> LENGTH: 352
<212> TYPE: PRT
<213> ORGANISM: Spinacia oleracea
<220> FEATURE:
<221> NAME/KEY: MISC_FEATURE
<222> LOCATION: (1)..(352)
<223> OTHER INFORMATION: PRK spinacia

<400> SEQUENCE: 12

Met Ser Gln Gln Gln Thr Ile Val Ile Gly Leu Ala Ala Asp Ser Gly
1               5                   10                  15

Cys Gly Lys Ser Thr Phe Met Arg Arg Leu Thr Ser Val Phe Gly Gly
                20                  25                  30

Ala Ala Glu Pro Pro Lys Gly Gly Asn Pro Asp Ser Asn Thr Leu Ile
                35                  40                  45

Ser Asp Thr Thr Thr Val Ile Cys Leu Asp Asp Phe His Ser Leu Asp
50                  55                  60

Arg Asn Gly Arg Lys Val Glu Lys Val Thr Ala Leu Asp Pro Lys Ala
65                  70                  75                  80

Asn Asp Phe Asp Leu Met Tyr Glu Gln Val Lys Ala Leu Lys Glu Gly
                85                  90                  95

Lys Ala Val Asp Lys Pro Ile Tyr Asn His Val Ser Gly Leu Leu Asp
                100                 105                 110

Pro Pro Glu Leu Ile Gln Pro Pro Lys Ile Leu Val Ile Glu Gly Leu
                115                 120                 125

His Pro Met Tyr Asp Ala Arg Val Arg Glu Leu Leu Asp Phe Ser Ile
                130                 135                 140

Tyr Leu Asp Ile Ser Asn Glu Val Lys Phe Ala Trp Lys Ile Gln Arg
145                 150                 155                 160

Asp Met Lys Glu Arg Gly His Ser Leu Glu Ser Ile Lys Ala Ser Ile
                165                 170                 175

Glu Ser Arg Lys Pro Asp Phe Asp Ala Tyr Ile Asp Pro Gln Lys Gln
                180                 185                 190

His Ala Asp Val Val Ile Glu Val Leu Pro Thr Glu Leu Ile Pro Asp
                195                 200                 205

Asp Asp Glu Gly Lys Val Leu Arg Val Arg Met Ile Gln Lys Glu Gly
                210                 215                 220

Val Lys Phe Phe Asn Pro Val Tyr Leu Phe Asp Glu Gly Ser Thr Ile
225                 230                 235                 240

Ser Trp Ile Pro Cys Gly Arg Lys Leu Thr Cys Ser Tyr Pro Gly Ile
                245                 250                 255

Lys Phe Ser Tyr Gly Pro Asp Thr Phe Tyr Gly Asn Glu Val Thr Val
                260                 265                 270
```

Val Glu Met Asp Gly Met Phe Asp Arg Leu Asp Glu Leu Ile Tyr Val
            275                 280                 285

Glu Ser His Leu Ser Asn Leu Ser Thr Lys Phe Tyr Gly Glu Val Thr
            290                 295                 300

Gln Gln Met Leu Lys His Gln Asn Phe Pro Gly Ser Asn Asn Gly Thr
305                 310                 315                 320

Gly Phe Phe Gln Thr Ile Ile Gly Leu Lys Ile Arg Asp Leu Phe Glu
                325                 330                 335

Gln Leu Val Ala Ser Arg Ser Thr Ala Thr Ala Thr Ala Lys Ala
                340                 345                 350

<210> SEQ ID NO 13
<211> LENGTH: 367
<212> TYPE: PRT
<213> ORGANISM: Escherichia coli
<220> FEATURE:
<221> NAME/KEY: MISC_FEATURE
<222> LOCATION: (1)..(367)
<223> OTHER INFORMATION: E. coli glycerol dehydrogenase (Ec_gldA) amino
      acid sequence

<400> SEQUENCE: 13

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
            35                  40                  45

Glu Lys Ser Phe Lys Asp Ala Gly Leu Val Val Glu Ile Ala Pro Phe
50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
            115                 120                 125

Val Ile Tyr Thr Asp Glu Gly Glu Phe Asp Arg Tyr Leu Leu Leu Pro
            130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
            195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

```
Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
        290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 14
<211> LENGTH: 584
<212> TYPE: PRT
<213> ORGANISM: Saccharomyces cerevisiae
<220> FEATURE:
<221> NAME/KEY: MISC_FEATURE
<222> LOCATION: (1)..(584)
<223> OTHER INFORMATION: S. cerevisiae dihydroxyacetone kinase (S.
      cerevisiae DAK1) amino acid sequence

<400> SEQUENCE: 14

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80

Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
        195                 200                 205

Asn Glu Lys Gln Met Glu Leu Gly Met Gly Ile His Asn Glu Pro Gly
    210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255
```

```
Val Lys Phe Asp Glu Asp Glu Val Val Leu Leu Val Asn Asn Leu
            260             265                 270
Gly Gly Val Ser Asn Phe Val Ile Ser Ser Ile Thr Ser Lys Thr Thr
            275                 280                 285
Asp Phe Leu Lys Glu Asn Tyr Asn Ile Thr Pro Val Gln Thr Ile Ala
            290                 295                 300
Gly Thr Leu Met Thr Ser Phe Asn Gly Asn Gly Phe Ser Ile Thr Leu
305                 310                 315                 320
Leu Asn Ala Thr Lys Ala Thr Lys Ala Leu Gln Ser Asp Phe Glu Glu
                325                 330                 335
Ile Lys Ser Val Leu Asp Leu Asn Ala Phe Thr Asn Ala Pro Gly
                340                 345                 350
Trp Pro Ile Ala Asp Phe Glu Lys Thr Ser Ala Pro Ser Val Asn Asp
                355                 360                 365
Asp Leu Leu His Asn Glu Val Thr Ala Lys Ala Val Gly Thr Tyr Asp
                370                 375                 380
Phe Asp Lys Phe Ala Glu Trp Met Lys Ser Gly Ala Glu Gln Val Ile
385                 390                 395                 400
Lys Ser Glu Pro His Ile Thr Glu Leu Asp Asn Gln Val Gly Asp Gly
                405                 410                 415
Asp Cys Gly Tyr Thr Leu Val Ala Gly Val Lys Gly Ile Thr Glu Asn
                420                 425                 430
Leu Asp Lys Leu Ser Lys Asp Ser Leu Ser Gln Ala Val Ala Gln Ile
                435                 440                 445
Ser Asp Phe Ile Glu Gly Ser Met Gly Gly Thr Ser Gly Gly Leu Tyr
450                 455                 460
Ser Ile Leu Leu Ser Gly Phe Ser His Gly Leu Ile Gln Val Cys Lys
465                 470                 475                 480
Ser Lys Asp Glu Pro Val Thr Lys Glu Ile Val Ala Lys Ser Leu Gly
                485                 490                 495
Ile Ala Leu Asp Thr Leu Tyr Lys Tyr Thr Lys Ala Arg Lys Gly Ser
                500                 505                 510
Ser Thr Met Ile Asp Ala Leu Glu Pro Phe Val Lys Glu Phe Thr Ala
            515                 520                 525
Ser Lys Asp Phe Asn Lys Ala Val Lys Ala Ala Glu Glu Gly Ala Lys
            530                 535                 540
Ser Thr Ala Thr Phe Glu Ala Lys Phe Gly Arg Ala Ser Tyr Val Gly
545                 550                 555                 560
Asp Ser Ser Gln Val Glu Asp Pro Gly Ala Val Gly Leu Cys Glu Phe
                565                 570                 575
Leu Lys Gly Val Gln Ser Ala Leu
            580

<210> SEQ ID NO 15
<211> LENGTH: 12
<212> TYPE: PRT
<213> ORGANISM: Spinacia oleracea
<220> FEATURE:
<221> NAME/KEY: MISC_FEATURE
<222> LOCATION: (1)..(12)
<223> OTHER INFORMATION: PRK motif

<400> SEQUENCE: 15

Asn Asn Asn Ala Thr Thr Gly Thr Thr Asn Asn Asn
1               5                   10
```

<210> SEQ ID NO 16
<211> LENGTH: 8
<212> TYPE: PRT
<213> ORGANISM: Spinacia oleracea
<220> FEATURE:
<221> NAME/KEY: MISC_FEATURE
<222> LOCATION: (1)..(8)
<223> OTHER INFORMATION: PRK motif

<400> SEQUENCE: 16

Thr Cys Gly Thr Thr Tyr Ala Gly
1               5

<210> SEQ ID NO 17
<211> LENGTH: 561
<212> TYPE: PRT
<213> ORGANISM: Punctularia strigosozonata
<220> FEATURE:
<221> NAME/KEY: MISC_FEATURE
<222> LOCATION: (1)..(561)
<223> OTHER INFORMATION: Punctularia strigosozonata glucoamylase

<400> SEQUENCE: 17

Ser Ser Lys Ser Val Ser Ala Tyr Ile Ser Ser Glu Ser Pro Ile Ala
1               5                   10                  15

His Ser Lys Leu Leu Asp Asn Ile Gly Pro Asp Gly Ala Lys Ala Pro
            20                  25                  30

Gly Ala Phe Pro Gly Val Val Ala Ser Pro Ser Thr Asp Asn Pro
        35                  40                  45

Asn Tyr Tyr Tyr Ser Trp Ile Arg Asp Ser Ser Leu Val Phe Lys Thr
 50                  55                  60

Leu Ile Asp Asp Tyr Val Asn Gly Lys Asn Thr Ser Lys Ser Leu Arg
65                  70                  75                  80

Ser Leu Ile Asp Asp Phe Val Thr Ala Ser Ser Val Phe Gln Gln Thr
                85                  90                  95

Pro Asn Pro Ser Gly Asn Val Ser Thr Gly Leu Gly Glu Pro Lys
            100                 105                 110

Phe Tyr Val Asn Glu Thr Ala Phe Leu Asp Ser Trp Gly Arg Pro Gln
        115                 120                 125

Arg Asp Gly Pro Ala Leu Arg Ser Thr Ala Leu Ile Thr Tyr Ala Asn
    130                 135                 140

Tyr Leu Leu Asp Asn Asp Asn Thr Thr Trp Val Lys Asp Thr Leu Trp
145                 150                 155                 160

Pro Ile Ile Glu Leu Asp Val Asn Tyr Val Ser Asp Phe Trp Asn Tyr
                165                 170                 175

Thr Thr Phe Asp Leu Trp Glu Glu Val Ala Ser Ser Phe Phe Thr
            180                 185                 190

Thr Ala Val Gln His Arg Ala Leu Arg Gln Ala Ser Lys Leu Ala Lys
        195                 200                 205

Thr Leu Asp Lys Thr Asp Asn Ile Asp Ser Trp Asn Thr Gln Ala Asp
    210                 215                 220

Asn Val Leu Cys Phe Leu Gln Ser Tyr Trp Asn Gly Ser Ala Ile Ile
225                 230                 235                 240

Ala Asn Thr Gly Gly Gly Arg Ser Gly Ile Asp Ala Asn Thr Val Leu
                245                 250                 255

Ala Ser Ile His Thr Phe Asp Ser Ser Ala Gly Cys Asp Ala Thr Thr
            260                 265                 270

Phe Gln Pro Cys Ser Asp Lys Ala Leu Ser Asn Leu Lys Val Tyr Val

```
            275                 280                 285
Asp Ala Phe Arg Ser Ile Tyr Glu Ile Asn Ser Gly Ile Asp Pro Asn
    290                 295                 300

Ala Ala Val Ala Thr Gly Arg Tyr Pro Glu Asp Val Phe Tyr Asp Gly
305                 310                 315                 320

Asn Pro Trp Tyr Leu Ala Thr Ala Ala Val Ala Glu Gln Leu Tyr Asp
                325                 330                 335

Ala Leu Tyr Val Trp Asn Thr Thr Gly Ser Leu Glu Ile Thr Asp Ile
            340                 345                 350

Ser Leu Pro Phe Phe Gln Gln Phe Asp Ser Asp Val Lys Thr Gly Thr
        355                 360                 365

Tyr Ser Asp Asp Asp Thr Phe Asp Ser Leu Ile Ser Ser Ile Gln Ser
    370                 375                 380

Phe Ala Asp Gly Phe Leu Glu Ile His Ala Lys Tyr Thr Pro Asp Asp
385                 390                 395                 400

Gly Ala Leu Ser Glu Glu Phe Ser Lys Thr Asp Gly Ser Gln Thr Ser
                405                 410                 415

Ala Ala Asp Leu Thr Trp Ser Tyr Ala Ala Ala Leu Thr Ala Phe Asp
            420                 425                 430

Ala Arg Ser Arg Asp Ala Ala Val Lys Trp Gly Ala Lys Gly Leu Gln
        435                 440                 445

Val Pro Asp Gly Thr Cys Lys Thr Asn Glu Gly Gly Asp Asp Gly Leu
    450                 455                 460

Gly Val Pro Val Thr Phe Leu Val Lys Asp Ala Glu Thr Val Glu Gly
465                 470                 475                 480

Gln Ser Val Tyr Ile Thr Gly Ser Ile Ala Thr Leu Lys Ser Trp Ser
                485                 490                 495

Pro Asp Asp Ala Leu Leu Met Ser Pro Ser Asp Tyr Pro Thr Trp Thr
            500                 505                 510

Leu Thr Val Asn Leu Ser Ala Ser Glu Ser Val Gln Tyr Lys Tyr Ile
        515                 520                 525

Lys Lys Asp Thr Ala Gly Thr Val Ile Trp Glu Ser Asp Pro Asn Asn
    530                 535                 540

Ser Leu Leu Val Pro Ser Gly Gly Ser Val Thr Thr Asp Thr Trp
545                 550                 555                 560

Arg

<210> SEQ ID NO 18
<211> LENGTH: 578
<212> TYPE: PRT
<213> ORGANISM: Punctularia strigosozonata
<220> FEATURE:
<221> NAME/KEY: MISC_FEATURE
<222> LOCATION: (1)..(578)
<223> OTHER INFORMATION: Punctularia strigosozonata glucoamylase with
      native signal sequence FGA09

<400> SEQUENCE: 18

Met Leu Ser Ser Leu Ile Val Ser Gly Leu Leu Ala Ser Gly Val Cys
1               5                   10                  15

Ala Ser Ser Lys Ser Val Ser Ala Tyr Ile Ser Ser Glu Ser Pro Ile
            20                  25                  30

Ala His Ser Lys Leu Leu Asp Asn Ile Gly Pro Asp Gly Ala Lys Ala
        35                  40                  45

Pro Gly Ala Phe Pro Gly Val Val Ala Ser Pro Ser Thr Asp Asn
    50                  55                  60
```

```
Pro Asn Tyr Tyr Tyr Ser Trp Ile Arg Asp Ser Ser Leu Val Phe Lys
 65                  70                  75                  80

Thr Leu Ile Asp Asp Tyr Val Asn Gly Lys Asn Thr Ser Lys Ser Leu
                 85                  90                  95

Arg Ser Leu Ile Asp Asp Phe Val Thr Ala Ser Ser Val Phe Gln Gln
                100                 105                 110

Thr Pro Asn Pro Ser Gly Asn Val Ser Thr Gly Gly Leu Gly Glu Pro
                115                 120                 125

Lys Phe Tyr Val Asn Glu Thr Ala Phe Leu Asp Ser Trp Gly Arg Pro
130                 135                 140

Gln Arg Asp Gly Pro Ala Leu Arg Ser Thr Ala Leu Ile Thr Tyr Ala
145                 150                 155                 160

Asn Tyr Leu Leu Asp Asn Asp Asn Thr Thr Trp Val Lys Asp Thr Leu
                165                 170                 175

Trp Pro Ile Ile Glu Leu Asp Val Asn Tyr Val Ser Asp Phe Trp Asn
                180                 185                 190

Tyr Thr Thr Phe Asp Leu Trp Glu Glu Val Ala Ser Ser Ser Phe Phe
                195                 200                 205

Thr Thr Ala Val Gln His Arg Ala Leu Arg Gln Ala Ser Lys Leu Ala
210                 215                 220

Lys Thr Leu Asp Lys Thr Asp Asn Ile Asp Ser Trp Asn Thr Gln Ala
225                 230                 235                 240

Asp Asn Val Leu Cys Phe Leu Gln Ser Tyr Trp Asn Gly Ser Ala Ile
                245                 250                 255

Ile Ala Asn Thr Gly Gly Gly Arg Ser Gly Ile Asp Ala Asn Thr Val
                260                 265                 270

Leu Ala Ser Ile His Thr Phe Asp Ser Ser Ala Gly Cys Asp Ala Thr
                275                 280                 285

Thr Phe Gln Pro Cys Ser Asp Lys Ala Leu Ser Asn Leu Lys Val Tyr
                290                 295                 300

Val Asp Ala Phe Arg Ser Ile Tyr Glu Ile Asn Ser Gly Ile Asp Pro
305                 310                 315                 320

Asn Ala Ala Val Ala Thr Gly Arg Tyr Pro Glu Asp Val Phe Tyr Asp
                325                 330                 335

Gly Asn Pro Trp Tyr Leu Ala Thr Ala Ala Val Ala Glu Gln Leu Tyr
                340                 345                 350

Asp Ala Leu Tyr Val Trp Asn Thr Thr Gly Ser Leu Glu Ile Thr Asp
                355                 360                 365

Ile Ser Leu Pro Phe Phe Gln Gln Phe Asp Ser Asp Val Lys Thr Gly
                370                 375                 380

Thr Tyr Ser Asp Asp Thr Phe Asp Ser Leu Ile Ser Ser Ile Gln
385                 390                 395                 400

Ser Phe Ala Asp Gly Phe Leu Glu Ile His Ala Lys Tyr Thr Pro Asp
                405                 410                 415

Asp Gly Ala Leu Ser Glu Glu Phe Ser Lys Thr Asp Gly Ser Gln Thr
                420                 425                 430

Ser Ala Ala Asp Leu Thr Trp Ser Tyr Ala Ala Leu Thr Ala Phe
                435                 440                 445

Asp Ala Arg Ser Arg Asp Ala Ala Val Lys Trp Gly Ala Lys Gly Leu
                450                 455                 460

Gln Val Pro Asp Gly Thr Cys Lys Thr Asn Glu Gly Gly Asp Asp Gly
465                 470                 475                 480
```

```
Leu Gly Val Pro Val Thr Phe Leu Val Lys Asp Ala Glu Thr Val Glu
                485                 490                 495

Gly Gln Ser Val Tyr Ile Thr Gly Ser Ile Ala Thr Leu Lys Ser Trp
            500                 505                 510

Ser Pro Asp Asp Ala Leu Leu Met Ser Pro Ser Asp Tyr Pro Thr Trp
            515                 520                 525

Thr Leu Thr Val Asn Leu Ser Ala Ser Glu Ser Val Gln Tyr Lys Tyr
            530                 535                 540

Ile Lys Lys Asp Thr Ala Gly Thr Val Ile Trp Glu Ser Asp Pro Asn
545                 550                 555                 560

Asn Ser Leu Leu Val Pro Ser Gly Gly Ser Val Thr Thr Asp Asp Thr
                565                 570                 575

Trp Arg

<210> SEQ ID NO 19
<211> LENGTH: 580
<212> TYPE: PRT
<213> ORGANISM: Artificial
<220> FEATURE:
<223> OTHER INFORMATION: Punctularia strigosozonata glucoamylase with Sc
      alpha mating factor signal sequence

<400> SEQUENCE: 19

Met Arg Phe Pro Ser Ile Phe Thr Ala Val Leu Phe Ala Ala Ser Ser
1               5                   10                  15

Ala Leu Ala Ser Ser Lys Ser Val Ser Ala Tyr Ile Ser Ser Glu Ser
            20                  25                  30

Pro Ile Ala His Ser Lys Leu Leu Asp Asn Ile Gly Pro Asp Gly Ala
        35                  40                  45

Lys Ala Pro Gly Ala Phe Pro Gly Val Val Ala Ser Pro Ser Thr
50                  55                  60

Asp Asn Pro Asn Tyr Tyr Tyr Ser Trp Ile Arg Asp Ser Ser Leu Val
65                  70                  75                  80

Phe Lys Thr Leu Ile Asp Asp Tyr Val Asn Gly Lys Asn Thr Ser Lys
                85                  90                  95

Ser Leu Arg Ser Leu Ile Asp Asp Phe Val Thr Ala Ser Ser Val Phe
            100                 105                 110

Gln Gln Thr Pro Asn Pro Ser Gly Asn Val Ser Thr Gly Gly Leu Gly
        115                 120                 125

Glu Pro Lys Phe Tyr Val Asn Glu Thr Ala Phe Leu Asp Ser Trp Gly
130                 135                 140

Arg Pro Gln Arg Asp Gly Pro Ala Leu Arg Ser Thr Ala Leu Ile Thr
145                 150                 155                 160

Tyr Ala Asn Tyr Leu Leu Asp Asn Asp Asn Thr Thr Trp Val Lys Asp
                165                 170                 175

Thr Leu Trp Pro Ile Ile Glu Leu Asp Val Asn Tyr Val Ser Asp Phe
            180                 185                 190

Trp Asn Tyr Thr Thr Phe Asp Leu Trp Glu Glu Val Ala Ser Ser Ser
        195                 200                 205

Phe Phe Thr Thr Ala Val Gln His Arg Ala Leu Arg Gln Ala Ser Lys
210                 215                 220

Leu Ala Lys Thr Leu Asp Lys Thr Asp Asn Ile Asp Ser Trp Asn Thr
225                 230                 235                 240

Gln Ala Asp Asn Val Leu Cys Phe Leu Gln Ser Tyr Trp Asn Gly Ser
                245                 250                 255
```

```
Ala Ile Ile Ala Asn Thr Gly Gly Gly Arg Ser Gly Ile Asp Ala Asn
        260                 265                 270
Thr Val Leu Ala Ser Ile His Thr Phe Asp Ser Ala Gly Cys Asp
        275                 280             285
Ala Thr Thr Phe Gln Pro Cys Ser Asp Lys Ala Leu Ser Asn Leu Lys
        290             295                 300
Val Tyr Val Asp Ala Phe Arg Ser Ile Tyr Glu Ile Asn Ser Gly Ile
305                 310             315                 320
Asp Pro Asn Ala Ala Val Ala Thr Gly Arg Tyr Pro Glu Asp Val Phe
                325                 330                 335
Tyr Asp Gly Asn Pro Trp Tyr Leu Ala Thr Ala Ala Val Ala Glu Gln
        340                 345                 350
Leu Tyr Asp Ala Leu Tyr Val Trp Asn Thr Thr Gly Ser Leu Glu Ile
        355                 360                 365
Thr Asp Ile Ser Leu Pro Phe Phe Gln Gln Phe Asp Ser Asp Val Lys
370                 375                 380
Thr Gly Thr Tyr Ser Asp Asp Thr Phe Asp Ser Leu Ile Ser Ser
385                 390                 395                 400
Ile Gln Ser Phe Ala Asp Gly Phe Leu Glu Ile His Ala Lys Tyr Thr
                405                 410                 415
Pro Asp Asp Gly Ala Leu Ser Glu Glu Phe Ser Lys Thr Asp Gly Ser
                420                 425                 430
Gln Thr Ser Ala Ala Asp Leu Thr Trp Ser Tyr Ala Ala Ala Leu Thr
        435                 440                 445
Ala Phe Asp Ala Arg Ser Arg Asp Ala Ala Val Lys Trp Gly Ala Lys
450                 455                 460
Gly Leu Gln Val Pro Asp Gly Thr Cys Lys Thr Asn Glu Gly Gly Asp
465                 470                 475                 480
Asp Gly Leu Gly Val Pro Val Thr Phe Leu Val Lys Asp Ala Glu Thr
                485                 490                 495
Val Glu Gly Gln Ser Val Tyr Ile Thr Gly Ser Ile Ala Thr Leu Lys
                500                 505                 510
Ser Trp Ser Pro Asp Asp Ala Leu Leu Met Ser Pro Ser Asp Tyr Pro
        515                 520                 525
Thr Trp Thr Leu Thr Val Asn Leu Ser Ala Ser Glu Ser Val Gln Tyr
        530                 535                 540
Lys Tyr Ile Lys Lys Asp Thr Ala Gly Thr Val Ile Trp Glu Ser Asp
545                 550                 555                 560
Pro Asn Asn Ser Leu Leu Val Pro Ser Gly Gly Ser Val Thr Thr Asp
                565                 570                 575
Asp Thr Trp Arg
        580
```

GLYCEROL FREE ETHANOL PRODUCTION

CROSS-REFERENCE TO RELATED APPLICATIONS

This application is the National Stage entry of International Application No. PCT/EP2018/075958, filed 25 Sep. 2018, which claims priority to European Patent Application No. 17193914.3, filed 29 Sep. 2017.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-519000_ST25.txt" created on 9 Mar. 2020, and 70,738 bytes in size) is submitted concurrently with the instant application, and the entire contents of the Sequence Listing are incorporated herein by reference.

BACKGROUND

Field

The invention relates to a recombinant cell suitable for ethanol production, the use of this cell for the preparation of ethanol, and a process for preparing fermentation product using said recombinant cell.

Description of Related Art

Microbial fermentation processes are applied for industrial production of a broad and rapidly expanding range of chemical compounds from renewable carbohydrate feedstocks. Especially in anaerobic fermentation processes, redox balancing of the cofactor couple NADH/NAD$^+$ can cause important constraints on product yields. This challenge is exemplified by the formation of glycerol as major by-product in the industrial production of—for instance—fuel ethanol by *Saccharomyces cerevisiae*, a direct consequence of the need to reoxidize NADH formed in biosynthetic reactions. Ethanol production by *Saccharomyces cerevisiae* is currently, by volume, the single largest fermentation process in industrial biotechnology, but various other compounds, including other alcohols, carboxylic acids, isoprenoids, amino acids etc., are currently produced in industrial biotechnological processes. For conventional fermentative production of fuel ethanol, such as from corn starch and cane sugar, sugars predominantly occur as dimers or polymers of hexose sugars, which upon release in monosaccharides after pretreatment and enzymatic hydrolysis by different forms of glucohydrolases can be efficiently and rapidly fermented by *Saccharomyces cerevisiae*. Cellulosic or second generation bioethanol is produced from e.g. lignocellulosic fractions of plant biomass that is hydrolyzed intro free monomeric sugars, such as hexoses and pentoses, for fermentation into ethanol. Apart from the sugar release during pretreatment and hydrolysis of the biomass, some toxic by-products are formed depending on several pretreatment parameters, such as temperature, pressure and pretreatment time. Various approaches have been proposed to improve the fermentative properties of organisms used in industrial biotechnology by genetic modification. A major challenge relating to the stoichiometry of yeast-based production of ethanol, but also of other compounds, is that substantial amounts of NADH-dependent side-products (in particular glycerol) are generally formed as a by-product, especially under anaerobic and oxygen-limited conditions or under conditions where respiration is otherwise constrained or absent. It has been estimated that, in typical industrial ethanol processes, up to about 4 wt % of the sugar feedstock is converted into glycerol (Nissen et al. Yeast 16 (2000) 463-474). Under conditions that are ideal for anaerobic growth, the conversion into glycerol may even be higher, up to about 10%.

Glycerol production under anaerobic conditions is primarily linked to redox metabolism. During anaerobic growth of *S. cerevisiae*, sugar dissimilation occurs via alcoholic fermentation. In this process, the NADH formed in the glycolytic glyceraldehyde-3-phosphate dehydrogenase reaction is re-oxidized by converting acetaldehyde, formed by decarboxylation of pyruvate to ethanol via NAD$^+$ dependent alcohol dehydrogenase. The fixed stoichiometry of this redox-neutral dissimilatory pathway causes problems when a net reduction of NAD$^+$ to NADH occurs elsewhere in metabolism (e.g. biomass formation). Under anaerobic conditions, NADH re-oxidation in *S. cerevisiae* is strictly dependent on reduction of sugar to glycerol. Glycerol formation is initiated by reduction of the glycolytic intermediate dihydroxyacetone phosphate (DHAP) to glycerol 3-phosphate (glycerol-3P), a reaction catalyzed by NAD$^+$ dependent glycerol 3-phosphate dehydrogenase. Subsequently, the glycerol 3-phosphate formed in this reaction is hydrolysed by glycerol-3-phosphatase to yield glycerol and inorganic phosphate. Consequently, glycerol is a major by-product during anaerobic production of ethanol by *S. cerevisiae*, which is undesired as it reduces overall conversion of sugar to ethanol. Further, the presence of glycerol in effluents of ethanol production plants may impose costs for waste-water treatment.

EP-A-16206564.3 describes a recombinant cell, preferably a yeast cell comprising one or more genes coding for an enzyme having glycerol dehydrogenase activity, one or more genes coding dihydroxyacetone kinase (E.C. 2.7.1.28 and/or E.C. 2.7.1.29); one or more genes coding for ribulose-1,5-biphosphate carboxylase oxygenase (EC 4.1.1.39, RuBisCO); and one or more genes coding for phosphoribulokinase (EC 2.7.1.19, PRK); and optionally one or more genes coding for a glycerol transporter. A disadvantage of such cell is that may give insufficient ethanol yield. Therefore, there is a need for improved cells with glycerol dehydrogenase, PRK, RubisCO, and DAK.

SUMMARY

In accordance with the present invention there is provided a recombinant yeast comprising a recombinant yeast comprising a nucleotide sequence coding for a glycerol dehydrogenase, a nucleotide sequence coding for a ribulose-1,5-biphosphate carboxylase oxygenase (EC 4.1.1.39); a nucleotide sequence coding for a phosphoribulokinasey (EC 2.7.1.19); a nucleotide sequence allowing the expression of a glucoamylase (EC 3.2.1.20 or 3.2.1.3); and optionally a nucleotide sequence coding for a glycerol transporter.

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "gene" or "nucleotide sequence", this means "at least one" of that gene or nucleotide sequence, e.g. "at least one gene" or "at least one nucleotide sequence" unless specified otherwise. The term 'or' as used herein is to be understood as 'and/or'.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the cell, in particular a yeast cell, and usually corresponds to an oxygen consumption of less than 5 mmol/l·h$^{-1}$, in particular to an oxygen consumption of less than 2.5 mmol/l·h$^{-1}$, or less than 1 mmol/l·h$^{-1}$. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant yeast" as used herein, refers to a yeast strain containing nucleic acid which is the result of one or more genetic modifications using recombinant DNA technique(s) and/or another mutagenic technique(s). In particular a recombinant yeast may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

In the context of this invention an "altered gene" has the same meaning as a mutated gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov, (as available on 14 Jun. 2016) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. "SEQ ID NO: X"), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2'SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "disruption" is meant (or includes) all nucleic acid modifications such as nucleotide deletions or substitutions, gene knock-outs, (other) which affect the translation or transcription of the corresponding polypeptide and/or which affect the enzymatic (specific) activity, its substrate specificity, and/or or stability. Such modifications may be targeted on the coding sequence or on the promotor of the gene.

In one aspect the invention provides a recombinant yeast comprising:
  a nucleotide sequence coding for a glycerol dehydrogenase,
  a nucleotide sequence coding for a ribulose-1,5-biphosphate carboxylase oxygenase (EC 4.1.1.39);
  a nucleotide sequence coding for a phosphoribulokinase (EC 2.7.1.19);
  a nucleotide sequence allowing the expression of a glucoamylase (EC 3.2.1.20 or 3.2.1.3); and optionally
  a nucleotide sequence coding for a glycerol transporter.

Glucoamylase, also referred to as amyloglucosidase, alpha-glucosidase, glucan 1,4-alpha glucosidase, maltase glucoamylase, and maltase-glucoamylase, catalyses at least the hydrolysis of terminal 1,4-linked alpha-D-glucose residues from non-reducing ends of amylose chains to release free D-glucose.

In an embodiment the glucoamylase has an amino acid sequence according to SEQ ID NO: 17 or is a functional homologue thereof having a sequence identity of at least 50%, preferably at least 60%, 70%, 75%, 80%, 85%, 90%, 95, 98%, or 99%. The polypeptide of SEQ ID NO: 17 encodes a "mature glucoamylase", referring to the enzyme in its final form after translation and any post-translational modifications, such as N-terminal processing, C-terminal truncation, glycosylation, phosphorylation, etc.

In an embodiment the nucleotide sequence allowing the expression of a glucoamylase encodes a polypeptide having an amino acid sequence of SEQ ID NO: 18 or a variant thereof having a sequence identity of at least 50%, preferably at least 60%, 70%, 75%, 80%, 85%, 90%, 95, 98%, or 99%. Amino acids 1-17 of the SEQ ID NO: 18 may encode for a signal sequence.

In another embodiment the nucleotide sequence allowing the expression of a glucoamylase encodes a polypeptide having an amino acid sequence of SEQ ID NO: 19 or a variant thereof having a sequence identity of at least 50%, preferably at least 60%, 70%, 75%, 80%, 85%, 90%, 95, 98%, or 99%. Amino acids 1-19 of the SEQ ID NO: 19 may encode for a signal sequence.

A signal sequence (also referred to as signal peptide, targeting signal, localization signal, localization sequence, transit peptide, leader sequence or leader peptide) can be present at the N-terminus of a polypeptide (here, the glucoamylase) where it signals that the polypeptide is to be excreted, for example outside the cell and into the media.

In an embodiment the glycerol dehydrogenase is a $NAD^+$ linked glycerol dehydrogenase (EC 1.1.1.6). Such enzyme may be from bacterial origin or for instance from fungal origin. An example is gldA from *E. coli*.

Alternatively, the enzyme having glycerol dehydrogenase activity is a $NADP^+$ linked glycerol dehydrogenase (EC 1.1.1.72).

When the recombinant yeast is used for ethanol production, which typically takes place under anaerobic conditions, $NAD^+$ linked glycerol dehydrogenase are preferred.

In an embodiment the recombinant yeast comprises one or more nucleotide sequences encoding a heterologous glycerol dehydrogenase represented by amino acid sequence SEQ ID NO: 1, 2, 3 or 13 or a functional homologue thereof a having sequence identity of at least 50%, preferably at least 60%, 70%, 75%, 80% 85%, 90%, 95%, 98% or 99%.

It is understood that the recombinant yeast has an endogenous nucleotide sequence coding a dihydroxy acetone kinase, such as a DAK1 gene. Such nucleotide sequence is preferably placed under control of a constitutive promoter. In an embodiment the recombinant yeast comprises one or more nucleic acid sequences encoding a dihydroxy acetone kinase represented by amino acid sequence according to SEQ ID NO: 4, 5, 6, or 14 or by a functional homologue thereof having a sequence identity of at least 50%, preferably at least 60%, 70%, 75%, 80%, 85%, 90%, 95, 98%, or 99%, which nucleotide sequence is preferably placed under control of a constitutive promoter. The dihydroxy acetone kinase may also have glyceraldehyde kinase activity.

The recombinant yeast optionally comprises a nucleotide sequence coding for a glycerol transporter. In this embodiment any glycerol that is externally available in the medium (e.g. from the backset in corn mash) or secreted after internal cellular synthesis may be transported into the cell and converted to ethanol. In an embodiment the recombinant yeast comprises one or more nucleic acid sequences encoding a heterologous glycerol transporter represented by amino acid sequence SEQ ID NO:7 or a functional homologue thereof having a sequence identity of at least 50%, preferably at least 60%, 70%, 75%, 80%, 85%, 90%, 95%, 98%, or 99%.

In an embodiment the recombinant yeast comprises a deletion or disruption of one or more endogenous nucleotide sequences encoding a glycerol exporter (e.g FPS1). In an embodiment the recombinant yeast comprises one or more nucleic acid sequences encoding a heterologous glycerol transporter represented by amino acid sequence SEQ ID NO: 8 or a functional homologue thereof having a sequence identity of at least 50%, preferably at least 60%, 70%, 75%, 80% 85%, 90%, 95%, 98% or 99%.

In another embodiment the recombinant yeast comprises a deletion or disruption of one or more endogenous nucleotide sequences encoding a glycerol kinase (EC 2.7.1.30). An example of such an enzyme is Gut1p.

In a further embodiment, the recombinant yeast naturally lacks enzymatic activity needed for the NADH-dependent glycerol synthesis or has reduced enzymatic activity needed for NADH-dependent glycerol synthesis compared to its corresponding wild type yeast, for example yeast belonging to the species *Brettanomyces intermedius*.

In an embodiment the recombinant yeast comprises a deletion or disruption of one or more endogenous nucleotide sequences encoding a glycerol 3-phosphate phosphohydrolase and/or encoding a glycerol-3-phosphate dehydrogenase. Such a deletion or disruption may result in decrease or removal of enzymatic activity. A deleted or disrupted glycerol-3-phosphate dehydrogenase preferably may belong to EC 1.1.5.3, such as GUT2, or to EC 1.1.1.8, such as PDP1 and or PDP2.

In embodiment the recombinant yeast is free of nucleotide sequences encoding NADH-dependent glycerol-3-phosphate dehydrogenase.

A reduced enzymatic activity can be achieved by modifying one or more nucleotide sequences encoding a NAD-dependent glycerol 3-phosphate dehydrogenase activity (GPD) or one or more nucleotide sequences encoding a glycerol phosphate phosphatase activity (GPP), such that the enzyme is expressed considerably less than in the wild-type or such that the nucleotide sequence encodes a polypeptide with reduced activity. Such modifications can be carried out using commonly known biotechnological techniques, and may in particular include one or more knock-out mutations or site-directed mutagenesis of promoter regions or coding regions of the structural genes encoding GPD and/or GPP. Alternatively, strains that are defective in glycerol production may be obtained by random mutagenesis followed by selection of strains with reduced or absent activity of GPD and/or GPP. Examples of genes in *S. cerevisiae* encoding GPD-activity are GPD1, GPD2, and GPP-activity are GPP1 and GPP2.

GPD and/or GPP may be entirely deleted, or at least a part is deleted which encodes a part of the enzyme that is essential for its activity. In particular, good results have been achieved with a *S. cerevisiae* cell, wherein the open reading frames of the GPD1 gene and of the GPD2 gene have been inactivated. Inactivation of a structural gene (target gene) can be accomplished by a person skilled in the art by synthetically synthesizing or otherwise constructing a DNA fragment consisting of a selectable marker gene flanked by DNA sequences that are identical to sequences that flank the region of the host cell's genome that is to be deleted. In particular, good results have been obtained with the inactivation of the GPD1 and GPD2 genes in Saccharomyces cerevisiae by integration of the marker genes kanMX and hphMX4. Subsequently this DNA fragment is transformed into a host cell. Transformed cells that express the dominant marker gene are checked for correct replacement of the region that was designed to be deleted, for example by a diagnostic polymerase chain reaction or Southern hybridization.

The Rubisco may be a single-subunit Rubisco or a Rubisco having more than one subunit. In particular, good results have been achieved with a single-subunit Rubisco. In particular, good results have been achieved with a form-II Rubisco, more in particular CbbM.

SEQ ID NO: 11 shows a suitable sequence of a suitable Rubisco. It is encoded by the cbbM gene from *Thiobacillus denitrificans*. An alternative to this Rubisco is a functional homologue of this Rubisco, in particular such functional homologue comprising an amino acid sequence having at least 80%, 85%, 90% or 95% sequence identity with SEQ ID NO: 11. Suitable natural Rubisco polypeptides are given in Table 1 of WO2014/129898.

The Rubisco is preferably functionally expressed in the microorganism, at least during use in an industrial process for preparing a compound of interest.

In an embodiment the functionally expressed Rubisco has an activity, defined by the rate of ribulose-1,5-bisphosphate-dependent $^{14}C$-bicarbonate incorporation by cell extracts of at least 1 nmol·min$^{-1}$·(mg protein)$^{-1}$, in particular an activity of at least 2 nmol·min$^{-1}$·(mg protein)$^{-1}$, more in particular an activity of at least 4 nmol·min$^{-1}$·(mg protein)$^{-1}$. The upper limit for the activity is not critical. In practice, the activity may be about 200 nmol·min$^{-1}$·(mg protein)$^{-1}$ or less, in particular 25 nmol·min$^{-1}$·(mg protein)$^{-1}$, more in particular 15 nmol·min$^{-1}$·(mg protein)$^{-1}$ or less, e.g. about 10 nmol·min$^{-1}$·(mg protein)$^{-1}$ or less. The conditions for an assay for determining this Rubisco activity are as found in Example 4 of WO2014/129898.

The inventors have found that the recombinant yeast cell of the invention having genes coding for a glycerol dehydrogenase, a RuBisCO, and a PRK may have suboptimal ethanol yield, as compared to similar cells without a glucoamylase.

In an embodiment the recombinant yeast comprises one or more nucleotide sequences, preferably a heterologous nucleotide sequences, coding for molecular chaperones, said chaperones preferably originating from a prokaryote, more preferably a bacterium, even more preferably *E. coli*.

Chaperones—when expressed—are preferably capable of functionally interacting with an enzyme in the microorganism, in particular with at least one of Rubisco and PRK. Chaperones are proteins that provide favourable conditions for the correct folding of other proteins, thus preventing aggregation. Newly made proteins usually must fold from a linear chain of amino acids into a three-dimensional form. Chaperonins belong to a large class of molecules that assist protein folding, called molecular chaperones. The energy to fold proteins is supplied by adenosine triphosphate (ATP). A review article about chaperones that is useful herein is written by Yébenes (2001); "Chaperonins: two rings for folding"; Hugo Yebenes et al. Trends in Biochemical Sciences, August 2011, Vol. 36, No. 8.

In an embodiment, the one or more chaperone is from a bacterium, more preferably from *Escherichia*, in particular *E. coli* GroEL and GroES from *E. coli* may in particular encoded in a microorganism according to the invention. Other preferred chaperones are chaperones from *Saccharomyces*, in particular *Saccharomyces cerevisiae* Hsp10 and Hsp60. If the chaperones are naturally expressed in an organelle such as a mitochondrion (examples are Hsp60 and Hsp10 of *Saccharomyces cerevisiae*) relocation to the cytosol can be achieved e.g. by modifying the native signal sequence of the chaperonins.

In eukaryotes the proteins Hsp60 and Hsp10 are structurally and functionally nearly identical to GroEL and GroES, respectively. Thus, it is contemplated that Hsp60 and Hsp10 from any eukaryotic cell may serve as a chaperone for the Rubisco. See Zeilstra-Ryalls J, Fayet O, Georgopoulos C (1991). "The universally conserved GroE (Hsp60) chaperonins". Annu Rev Microbiol. 45: 301-25. doi:10.1146/annurev.mi.45.100191.001505. PMID 1683763 and Horwich A L, Fenton W A, Chapman E, Farr G W (2007). "Two Families of Chaperonin: Physiology and Mechanism". Annu Rev Cell Dev Biol. 23: 115-45. doi:10.1146/annurev.cellbio.23.090506.123555. PMID 17489689.

As an alternative to GroEL a functional homologue of GroEL may be present, in particular a functional homologue comprising an amino acid sequence having at least 70%, 75%, 80%, 85%, 90% or 95% sequence identity with SEQ ID NO: 10. Suitable natural chaperones polypeptides homologous to SEQ ID NO: 10 are given in Table 4 of WO2014/129898.

As an alternative to GroES a functional homologue of GroES may be present, in particular a functional homologue comprising an amino acid sequence having at least 70%, 75%, 80%, 85%, 90% or 95% sequence identity with SEQ ID NO: 9. Suitable natural chaperones polypeptides homologous to SEQ ID NO: 9 are given in Table 3 of WO2014/129898.

In an embodiment, a 10 kDa chaperone from Table 3 of WO2014/129898 is combined with a matching 60 kDa chaperone from Table 4 from WO2014/129898 of the same organism genus or species for expression in the host. For instance: >gi|189189366|ref|XP_001931022.1|:71-168 10 kDa chaperonin [Pyrenophora tritici-repentis] expressed together with matching >gi|189190432|ref|XP_001931555.1| heat shock protein 60, mitochondrial precursor [Pyrenophora tritici-repentis Pt-1C-BFP].

All other combinations from Table 3 and 4 of WO2014/129898 similarly made with same organism source are also available to the skilled person for expression.

In an embodiment the PRK is originating from a plant selected from *Caryophyllales*, in particular from *Amaranthaceae*, in particular from *Spinacia*.

In an embodiment the recombinant yeast comprises one or more nucleic acid sequences encoding a PRK represented by amino acid sequence represented by SEQ ID NO: 12 or by a functional homologue thereof having sequence identity of at least 50%, preferably at least 60%, 70%, 75%, 80% 85%, 90%, 95%, 98%, or 99%.

A functionally expressed phosphoribulokinase (PRK, EC 2.7.1.19) is capable of catalysing the chemical reaction:

$$ATP + \text{D-ribulose 5-phosphate} \rightarrow ADP + \text{D-ribulose 1,5-bisphosphate} \qquad (I)$$

Thus, the two substrates of this enzyme are ATP and D-ribulose 5-phosphate, whereas its two products are ADP and D-ribulose 1,5-bisphosphate.

PRK belongs to the family of transferases, specifically those transferring phosphorus-containing groups (phosphotransferases) with an alcohol group as acceptor. The systematic name of this enzyme class is ATP:D-ribulose-5-phosphate 1-phosphotransferase. Other names in common use include phosphopentokinase, ribulose-5-phosphate kinase, phosphopentokinase, phosphoribulokinase (phosphorylating), 5-phosphoribulose kinase, ribulose phosphate kinase, PKK, PRuK, and PRK. This enzyme participates in carbon fixation.

The PRK can be from a prokaryote or a eukaryote. Good results have been achieved with a PRK originating from a eukaryote. Preferably the eukaryotic PRK originates from a plant selected from *Caryophyllales*, in particular from *Amaranthaceae*, more in particular from *Spinacia*.

As an alternative to PRK from *Spinacia* a functional homologue of PRK from *Spinacia* may be present, in particular a functional homologue comprising a sequence having at least 70%, 75%, 80%. 85%, 90% or 95% sequence identity with the PRK from *Spinacia*.

The one or more PRK nucleotide sequences may be under the control of a promoter (the "PRK promoter") that enables higher expression under anaerobic conditions than under aerobic conditions.

In an embodiment the PRK promoter is ROX1 repressed. ROX1 is herein haeme-dependent repressor of hypoxic gene(s); that mediates aerobic transcriptional repression of hypoxia induced genes such as COX5b and CYC7; the repressor function is regulated through decreased promoter occupancy in response to oxidative stress; and contains an HMG domain that is responsible for DNA bending activity; involved in the hyperosmotic stress resistance. ROX1 is regulated by oxygen.

According to Kwast et al. (in: Genomic Analysis of Anaerobically induced genes in *Saccharomyces cerevisiae*: Functional roles of ROX1 and other factors in mediating the anoxic response, 2002, Journal of bacteriology vol 184, no 1 p 250-265): "Although Rox1 functions in an $O_2$-independent manner, its expression is oxygen (haeme) dependent, activated by the haeme-dependent transcription factor Hap1 [Keng, T. 1992. HAP1 and ROX1 form a regulatory pathway in the repression of HEM13 transcription in *Saccharomyces cerevisiae*. Mol. Cell. Biol. 12: 2616-2623]. Thus, as oxygen levels fall to those that limit haeme biosynthesis [Labbe-Bois, R., and P. Labbe. 1990. Tetrapyrrole and heme biosynthesis in the yeast *Saccharomyces cerevisiae*, p. 235-285. In H. A. Dailey (ed.), Biosynthesis of heme and chlorophylls. McGraw-Hill, New York, N.Y.], ROX1 is no longer transcribed [Zitomer, R. S., and C. V. Lowry. 1992. Regulation of gene expression by oxygen in *Saccharomyces cerevisiae*. Microbiol. Rev. 56:1-11], its protein levels fall [Zitomer, R. S., P. Carrico, and J. Deckert. 1997. Regulation of hypoxic gene expression in yeast. Kidney Int 51:507-513], and the genes it regulates are de-repressed."

In an embodiment, the PRK promoter is ROX1-repressed. In an embodiment, the PRK promoter has one or more ROX1 binding motif.

In an embodiment, the PRK promoter comprises in its sequence one or more of the motif according to SEQ ID NO: 15.

In an embodiment, the PRK promoter is the native promoter of a nucleotide sequence selected from the list consisting of: FET4, ANB1, YHR048W, DAN1, AAC3, TIR2, DIPS, HEM13, YNR014W, YAR028W, FUN 57, COX5B, OYE2, SUR2, FRDS1, PIS1, LAC1, YGR035C, YAL028W, EUG1, HEM14, ISU2, ERG26, YMR252C and SML1, in particular FET4, ANB1, YHR048W, DAN1, AAC3, TIR2, DIPS and HEM13.

In an embodiment, the PRK promoter comprises in its sequence one or more of the motif according to TCGTTYAG and/or according to SEQ ID NO: 16.

In particular such PRK promoter is native promoter of a DAN, TIR or PAU gene. In an embodiment, the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W, YOR394W, YHL046C, YMR325W, YAL068C, YPL282C, PAU2, PAU4, in particular the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, YLL025W.

In an embodiment, the promoter has a PRK expression ratio anaerobic/aerobic of 2 or more, 3 or more, 4 or more, 5 or more, 6 or more, 7 or more, 8 or more, 9 or more, 10 or more, 20 or more or 50 or more.

As used herein "promoter" is a DNA sequence that directs the transcription of a (structural) gene, herein in particular one or more phosphoribulokinase gene. The promoter enables higher expression during anaerobic conditions than under aerobic conditions.

In an embodiment, the PRK promoter may be a synthetic oligonucleotide. It may be a product of artificial oligonucleotide synthesis. Artificial oligonucleotide synthesis is a method in synthetic biology that is used to create artificial oligonucleotides, such as genes, in the laboratory. Commercial gene synthesis services are now available from numerous companies worldwide, some of which have built their business model around this task. Current gene synthesis approaches are most often based on a combination of organic chemistry and molecular biological techniques and entire genes may be synthesized "de novo", without the need for precursor template DNA.

In an embodiment, the promoter is located in the 5' region of a the PRK gene, In an embodiment it is located proximal to the transcriptional start site of PRK gene.

The recombinant yeast may be selected from Saccharomycetaceae, in particular from the group of *Saccharomyces*, such as *Saccharomyces cerevisiae*; *Kluyveromyces*, such as *Kluyveromyces marxianus*; *Pichia*, such as *Pichia stipitis* or *Pichia angusta*; *Zygosaccharomyces*, such as *Zygosaccharomyces bailii*; and *Brettanomyces*, such as *Brettanomyces intermedius, Issatchenkia*, such as *Issatchenkia orientalis* and *Hansenula*.

The PRK promoter may have a PRK expression ratio anaerobic/aerobic of 2 or more, 3 or more, 4 or more, 5 or more, 6 or more, 7 or more, 8 or more, 9 or more, 10 or more, 20 or more or 50 or more.

In an embodiment the PRK promoter is a synthetic oligonucleotide. The PRK promoter preferably enables expression only during anaerobic conditions.

A suitable PRK promotor is ANB1 and/or DAN1 as mentioned in EP16174382.8.

The recombinant yeast may contain genes of a pentose metabolic pathway non-native to the cell and/or that allow the recombinant cell to convert pentose(s). In one embodiment, the recombinant yeast may comprise one or two or more copies of one or more xylose isomerases and/or one or two or more copies of one or more xylose reductase and xylitol dehydrogenase genes, allowing the recombinant yeast convert xylose. In an embodiment thereof, these genes may be integrated into the recombinant cell genome. In another embodiment, the recombinant yeast comprises the genes araA, araB and araD. It is then able to ferment arabinose. In one embodiment the recombinant yeast comprises xylA-gene, XYL1 gene and XYL2 gene and/or XKS1-gene, to allow the recombinant yeast to ferment xylose; deletion of the aldose reductase (GRE3) gene; overexpression of one or more PPP-genes, e.g. TAL1, TAL2, TKL1, TKL2, RPE1 and RKI1 to allow the increase of the flux through the pentose phosphate path-way in the cell, and/or overexpression of GAL2 and/or deletion of GAL80. Thus though inclusion of the above genes, suitable pentose or other metabolic pathway(s) may be introduced in the recombinant yeast that were non-native in the (wild type) recombinant yeast.

In an embodiment, the following genes may be introduced in the recombinant yeast by introduction into a host cell:
1) a set consisting of PPP-genes TAL1, TKL1, RPE1 and RKI1, optionally under control of strong constitutive promoter;
2) a set consisting of a xylA-gene under under control of strong constitutive promoter;
3) a set comprising a XKS1-gene under control of strong constitutive promoter,
4) a set consisting of the bacterial genes araA, araB and araD under control of a strong constitutive promoter,
5) deletion of an aldose reductase gene The above cells may be constructed using known recombinant expression techniques. The co-factor modification may be effected before, simultaneous or after any of the modifications 1-5 above.

The recombinant yeast may be subjected to evolutionary engineering to improve its properties. Evolutionary engineering processes are known processes. Evolutionary engineering is a process wherein industrially relevant phenotypes of a microorganism, herein the recombinant yeast, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5(2005) 925-934, WO2008041840 and WO2009112472. After the evolutionary engineering the resulting pentose fermenting recombinant cell is isolated. The isolation may be executed in any known manner, e.g. by separation of cells from a recombinant cell broth used in the evolutionary engineering, for instance by taking a cell sample or by filtration or centrifugation.

In an embodiment, the recombinant yeast is marker-free. As used herein, the term "marker" refers to a gene encoding a trait or a phenotype which permits the selection of, or the screening for, a host cell containing the marker. Marker-free means that markers are essentially absent in the recombinant yeast. Being marker-free is particularly advantageous when antibiotic markers have been used in construction of the recombinant yeast and are removed thereafter. Removal of markers may be done using any suitable prior art technique, e.g. intramolecular recombination.

In one embodiment, the recombinant yeast is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant S. cerevisiae strain ATCC 26602 was selected.

To increase the likelihood that enzyme activity is expressed at sufficient levels and in active form in the recombinant yeast, the nucleotide sequence encoding these enzymes, as well as the Rubisco enzyme and other enzymes of the disclosure are preferably adapted to optimise their codon usage to that of the recombinant yeast in question.

The adaptiveness of a nucleotide sequence encoding an enzyme to the codon usage of a cell may be expressed as codon adaptation index (CAI). The codon adaptation index is herein defined as a measurement of the relative adaptiveness of the codon usage of a gene towards the codon usage of highly expressed genes in a particular cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in the host cell in question such as e.g. S. cerevisiae cells.

The invention further provides the use of a recombinant yeast according to the invention for preparation of ethanol.

The present invention also provides a process to produce a fermentation product comprising:
fermenting a composition comprising a fermentable carbohydrate, in particular selected from the group of glucose, fructose, sucrose, maltose, xylose, arabinose, galactose and mannose under anaerobic conditions in the presence of a recombinant yeast according to the invention; and
recovering the ethanol.

In an embodiment one such composition is a biomass hydrolysate. Such biomass hydrolysate may be a lignocellulosic biomass hydrolysate. Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins). Lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

In another embodiment such composition is a pre-treated cornstover hydrolysate. Another preferred composition is a corn fiber hydrolysate, which is optionally pre-treated. In yet another embodiment such composition is a starch hydrolysate, such as a corn starch hydrolysate.

In the context of the invention a "hydrolysate" means a polysaccharide that has been depolymerized through the addition of water to form mono and oligosaccharide sugars. Hydrolysates may be produced by enzymatic or acid hydrolysis of the polysaccharide-containing material.

In an embodiment the fermentable carbohydrate is obtained from starch, lignocellulose, and/or pectin.

The starch, lignocellulose, and/or pectin may be contacted with an enzyme composition, wherein one or more sugar is produced, and wherein the produced sugar is fermented to give a fermentation product, wherein the fermentation is conducted with a recombinant yeast of the invention.

The process is particularly useful when glycerol is fed externally to the process, such as crude glycerol from transesterification-based biodiesel production or recirculation of backset, which is then taken up and converted to ethanol by the claimed recombinant yeast.

In an embodiment the composition comprises an amount of undissociated acetic acid of 10 mM or less.

The inventors have found that a recombinant yeast of the invention, specifically a S. cerevisiae cell is particularly sensitive towards acetic acid, as compared to non-recombinant cells. They have surprisingly found that the ethanol yield rapidly decreases when the composition contains more than 10 mM undissociated acetic acid, and that in order to avoid or lessen the negative effect of acetic acid the process should be performed with a composition having an amount of undissociated acetic acid of 10 mM or less, preferably 9 mM or less, 8 mM or less, 7 mM or less, 6 mM or less, 5 mM or less, 4 mM or less, 3 mM or less, 2 mM or less, 1 mM or less.

In an embodiment the composition has an initial undissociated acetic acid of 10 mM or less. In another embodiment, the amount of undissociated acetic acid is 10 mM or less throughout the process.

The lower amount of undissociated acetic acid is less important. In one embodiment, the composition is free of undissociated acetic acid.

In an embodiment, the lower limit of the amount of undissociated acetic acid is 50 µM or more, 55 µM or more, 60 µM or more, 70 µM or more, 80 µM or more, 90 µM or more, 100 µM or more.

The skilled person appreciates that the amount of undissociated acetic acid depends inter alia on the total amount of acetic acid in the composition (protonated and dissociated) as well on the pH.

In one embodiment the amount of undissociated acetic acid is maintained at a value of at 10 mM by adjusting the pH, e.g. by adding a base.

The process may comprise the step of monitoring the pH. The pH of the composition is preferably kept between 4.2 and 5.2, preferably between 4.5 and 5.0. The lower pH is preferably such that the amount of undissociated acetic acid is 10 mM or less, which inter alia depends on the total amount of acetic acid in the composition.

The skilled person knows how to provide or select a composition having an amount of undissociated acetic acid 10 mM or less. For example, he/she may measure the amount of undissociated acetic acid in a composition and select only those compositions which have an amount of undissociated acetic acid of 10 mM or less.

Alternatively, if the amount of undissociated acetic acid in a composition exceeds 10 mM, the process may comprise, prior to the fermentation step, adding a base (such as NaOH or KOH) until the amount of undissociated acetic acid in a composition has reached a value of 10 mM or less.

The amount of undissociated acetic acid may be analysed by HPLC. HPLC generally measures all acetic acid (i.e. both undissociated, i.e. protonated form and dissociated form of acetic acid) because the mobile phase is typically acidified. In order to measure the amount of undissociated acetic acid in the composition, a suitable approach is to measure the (total) amount of acetic acid of the composition as-is, measure the pH of the composition, and calculate the amount of undissociated acetic acid using the pKa of acetic acid.

The invention claimed is:

1. A recombinant yeast comprising:

a nucleotide sequence coding for a glycerol dehydrogenase, a nucleotide sequence coding for a ribulose-1,5-biphosphate carboxylase oxygenase (EC 4.1.1.39);

a nucleotide sequence coding for a phosphoribulokinase (EC 2.7.1.19);

a nucleotide sequence allowing the expression of a glucoamylase (EC 3.2.1.20 or 3.2.1.3), the glucoamylase comprising the amino acid sequence according to SEQ ID NO: 17 or a functional homologue thereof having a sequence identity of at least 70% to SEQ ID NO: 17; and optionally a nucleotide sequence coding for a glycerol transporter.

2. The recombinant yeast according to claim 1 which comprises a deletion or disruption of one or more endogenous nucleotide sequences encoding a glycerol exporter.

3. The recombinant yeast according to claim 2, wherein the deletion or disruption of one or more endogenous nucleotide sequences encoding a glycerol exporter comprises a deletion or disruption of one or more endogenous nucleotide sequences encoding a FPS1 glycerol exporter.

4. The recombinant yeast according to claim 1 which comprises a deletion or disruption of one or more endogenous nucleotide sequences encoding a glycerol kinase (EC 2.7.1.30).

5. The recombinant yeast which according to claim 1 which comprises a deletion or disruption of one or more endogenous nucleotide sequences encoding a glycerol-3-phosphate dehydrogenase (GPD1/2).

6. The recombinant yeast according to claim 1 which comprises a deletion or disruption of one or more endogenous nucleotide sequences encoding a glycerol 3-phosphate phosphohydrolase (GPP1/2).

7. The recombinant yeast according to claim 1 which is a *Saccharomyces*, optionally *Saccharomyces cerevisiae*.

8. The recombinant yeast according to claim 1 further comprising one or more nucleotide sequences, coding for molecular chaperones from *E. coli* which are selected from the group consisting of GroEL, GroES, functional homologues of GroEL, and functional homologues of GroES.

9. A product comprising the recombinant yeast according to claim 1 for preparation of ethanol and/or succinic acid.

10. A process for production of ethanol comprising:
fermenting a composition comprising a fermentable carbohydrate under anaerobic conditions in the presence of a recombinant yeast according to claim 1; and
recovering the ethanol.

11. The process according to claim 10, wherein the fermentable carbohydrate is obtained from starch, lignocellulose, and/or pectin.

12. The process according to claim 10, wherein said composition comprises an amount of undissociated acetic acid of 10 mM or less.

13. The process according to claim 10 wherein said composition comprises an amount of undissociated acetic acid of between 50 μM and 10 mM.

14. The process according to claim 10, wherein the fermentable carbohydrate is selected from the group of glucose, fructose, sucrose, maltose, xylose, arabinose, galactose, and mannose.

* * * * *